United States Patent
Malcolm

(10) Patent No.: US 12,357,704 B2
(45) Date of Patent: Jul. 15, 2025

(54) TAILORED HYPOIMMUNE NANOVESICULAR DELIVERY SYSTEMS FOR CANCER TUMORS

(71) Applicant: Thomas Malcolm, Andover, NJ (US)

(72) Inventor: Thomas Malcolm, Andover, NJ (US)

(73) Assignee: Thomas Malcolm, Andover, NJ (US)

( * ) Notice: Subject to any disclaimer, the term of this patent is extended or adjusted under 35 U.S.C. 154(b) by 905 days.

(21) Appl. No.: 17/605,214

(22) PCT Filed: May 6, 2020

(86) PCT No.: PCT/US2020/031616
§ 371 (c)(1),
(2) Date: Oct. 20, 2021

(87) PCT Pub. No.: WO2020/227369
PCT Pub. Date: Nov. 12, 2020

(65) Prior Publication Data
US 2022/0218842 A1 Jul. 14, 2022

Related U.S. Application Data

(60) Provisional application No. 62/843,713, filed on May 6, 2019.

(51) Int. Cl.
*A61K 47/69* (2017.01)
*A61K 9/50* (2006.01)
*C07K 14/725* (2006.01)

(52) U.S. Cl.
CPC ........ *A61K 47/6901* (2017.08); *A61K 9/5068* (2013.01); *C07K 14/7051* (2013.01); *C07K 2317/622* (2013.01); *C07K 2319/33* (2013.01); *C12N 2501/515* (2013.01); *C12N 2506/45* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 10,675,244 B2 | 6/2020 | Gho et al. | |
| 2006/0057192 A1 | 3/2006 | Kane | |
| 2008/0166319 A1 | 7/2008 | Schreiber et al. | |
| 2016/0243192 A1 | 8/2016 | Seeger et al. | |
| 2017/0080104 A1 | 3/2017 | Irvine et al. | |
| 2019/0024065 A1 | 1/2019 | Delacote et al. | |
| 2020/0208157 A1 | 7/2020 | Guo et al. | |
| 2022/0040106 A1 | 2/2022 | Malcolm et al. | |
| 2024/0307317 A1 | 9/2024 | Malcolm et al. | |

FOREIGN PATENT DOCUMENTS

| | | | |
|---|---|---|---|
| EP | 1447079 A1 | 8/2004 | |
| WO | WO 2015/002956 A1 | 1/2015 | |
| WO | WO 2018/015535 A1 | 1/2018 | |
| WO | WO 2018/029656 A2 | 2/2018 | |
| WO | WO 2018/175636 A2 | 9/2018 | |
| WO | WO-2018208728 A1 * | 11/2018 | ............ A61K 35/12 |
| WO | WO 2019/133934 A2 | 7/2019 | |
| WO | WO 2020/018620 A1 | 1/2020 | |
| WO | WO 2021/003445 A1 | 1/2021 | |
| WO | WO 2021/076630 A1 | 4/2021 | |
| WO | WO 2021/189047 A2 | 9/2021 | |
| WO | WO 2021/223659 A1 | 11/2021 | |
| WO | WO 2021/231884 A1 | 11/2021 | |
| WO | WO 2022/076596 A1 | 4/2022 | |
| WO | WO 2022/087019 A1 | 4/2022 | |
| WO | WO 2022/250880 A1 | 12/2022 | |

OTHER PUBLICATIONS

Willms et al., Extracellular vesicle heterogeneity: subpopulations, isolation techniques, and diverse functions in cancer progression. Frontiers in Immunology (2018), 9:738, 1-17 (Year: 2018).*
Van Dommelen et al., Microvesicles and exosomes: opportunities for cell-derived membrane vesicles in drug delivery. Journal of Controlled Release (2012), 161: 635-644 (Year: 2012).*
Cao et al., Seneca Valley virus attachment and uncoating mediated by its receptor anthrax toxin receptor 1. PNAS (2018), 115: 13087-13092 (Year: 2018).*
Deuse et al., Hypoimmunogenic derivatives of induced pluripotent stem cells evade immune rejection in fully immunocompetent allogeneic recipients. Nature Biotechnology (2019), 37: 252-258 (Year: 2019).*
Jalil et al., Suppressing or Enhancing Macrophage Engulfment through the Use of CD47 and Related Peptides. Bioconjugate chemistry (2022), 33: 1989-1995 (Year: 2022).*
Bonilla W.V. et al. Heterologous arenavirus vector prime-boost overrules self-tolerance for efficient tumor-specific CD8 T cell attack. Cell Rep Med. Mar. 3, 2021;2(3):100209.
Chen Y. et al. Expression of ssDNA in mammalian cells. BioTechniques. Jan. 2003;34(1):167-71.
Chmielewski M et al. TRUCKs: the fourth generation of CARs. Expert Opin Biol Ther. 2015;15(8):1145-54.

(Continued)

*Primary Examiner* — Celine X Qian
*Assistant Examiner* — Catherine Konopka
(74) *Attorney, Agent, or Firm* — Morgan, Lewis & Bockius LLP

(57) ABSTRACT

Hypoimmunogenic induced pluripotent stem cell (iPSC)-derived biomimetic nanovesicles (hypo-bioNVs) including tailored chimeric antigen receptor (CARs) which can recognize target biomarkers through an antibody fragment scFV region or by a viral epitope recognition receptor (VERR). A method of making hypo-bioNVs. A method of treating an individual with cancer, by administering the hypo-bioNVs to an individual, targeting cancer cells, and treating the cancer. A method of targeting cells in an individual, by administering the hypo-bioNVs to an individual, and targeting cells to be destroyed or treated.

20 Claims, 10 Drawing Sheets

(56) References Cited

OTHER PUBLICATIONS

Curiel D. et al. Adenovirus enhancement of transferrin-polylysine-mediated gene delivery. Proc Natl Acad Sci U S A. Oct. 1, 1991;88(19):8850-4.
Davis, et al. Direct gene transfer into skeletal muscle in vivo: factors affecting efficiency of transfer and stability of expression. Hum Gene Ther. Apr. 1993;4(2):151-9.
Deuse T. et al. Hypoimmunogenic derivatives of induced pluripotent stem cells evade immune rejection in fully immunocompetent allogeneic recipients. Nat Biotechnol. Mar. 2019;37(3):252-258.
Fu W. et al. CAR exosomes derived from effector CAR-T cells have potent antitumour effects and low toxicity. Nat Commun. Sep. 25, 2019;10(1):4355.
Gandhapudi S. et al. Antigen Priming with Enantiospecific Cationic Lipid Nanoparticles Induces Potent Antitumor CTL Responses through Novel Induction of a Type I IFN Response. J Immunol. Jun. 15, 2019;202(12):3524-3536.
Geller A.I. et al. An HSV-1 vector expressing tyrosine hydroxylase causes production and release of L-dopa from cultured rat striatal cells. J. Neurochem. Feb. 1995;64(2):487-96.
Geller A.I. et al., Long-term increases in neurotransmitter release from neuronal cells expressing a constitutively active adenylate cyclase from a herpes simplex virus type 1 vector. Proc Natl. Acad. Sci.: U.S.A. Aug. 15, 1993;90(16):7603-7.
Geller A.I., et al. Infection of cultured central nervous system neurons with a defective herpes simplex virus 1 vector results in stable expression of *Escherichia coli* beta-galactosidase. Proc Natl. Acad. Sci USA: Feb. 1990;87(3):1149-53.
Goh W.J. et al. Bioinspired Cell-Derived Nanovesicles versus Exosomes as Drug Delivery Systems: a Cost-Effective Alternative. Sci Rep. Oct. 30, 2017;7(1):14322.
Goh W.J. et al. Doxorubicin-loaded cell-derived nanovesicles: an alternative targeted approach for anti-tumor therapy. Int J Nanomedicine. Apr. 4, 2017;12:2759-2767.
Quantin, et al. Adenovirus as an expression vector in muscle cells in vivo. Proc. Natl. Acad. Sci. USA, Apr. 1, 1992;89(7):2581-4.
Singh N. et al. Antigen-independent activation enhances the efficacy of 4-1BB-costimulated CD22 CAR T cells. Nat Med. May 2021;27(5):842-850.
Sonntag F. et al. AAV type 2 capsids with externalized VP1/VP2 trafficking domains are generated prior to passage through the cytoplasm and are maintained until the uncoating occurs in the nucleus. J Virol. Nov. 2006;80(22):11040-54.
Stahnke S. et al. Intrinsic phospholipase A2 activity of AAV is involved in endosomal escape of incoming particles. Virology. Jan. 5, 2011;409(1):77-83.
Stratford-Perricadet, et al. Widespread long-term gene transfer to mouse skeletal muscles and heart. J. Clin. Invest. Aug. 1992;90(2):626-30. J Clin Invest.
Thalhauser S. et al. Presentation of HIV-1 Envelope Trimers on the Surface of Silica Nanoparticles. J Pharm Sci. Jan. 2020;109(1):911-921.
Wolfs J. et al. Biasing genome-editing events toward precise length deletions with an RNA-guided TevCas9 dual nuclease. Proc Natl Acad Sci USA. Dec. 27, 2016;113(52):14988-14993.
Wu J.Y. et al. Exosome-Mimetic Nanovesicles from Hepatocytes promote hepatocyte proliferation in vitro and liver regeneration in vivo. Sci Rep. Feb. 6, 2018;8(1):2471.
Yang H et al. PAM-Dependent Target DNA Recognition and Cleavage by C2c1 CRISPR-Cas Endonuclease. Cell. Dec. 1, 20165;167(7):1814-1828.e12.
Zadori Z et al. A viral phospholipase A2 is required for parvovirus infectivity. Dev Cell. Aug. 2001;1(2):291-302.
Zhang P. et al. Genetically Engineered Liposome-like Nanovesicles as Active Targeted Transport Platform. Adv Mater. Feb. 2018;30(7).
Mei Z. et al. MUC1 as a target for CART therapy in head and neck squamous cell carcinoma. Cancer Med. Jan. 2020;9(2):640-652.
Wang K. et al. GD2-specific Car T cells encapsulated in an injectable hydrogel control retinoblastoma and preserve vision. Nat Cancer. Oct. 2020;1(10):990-997.
Bose, et al., "Bioengineered stem cell membrane functionalized nanocarriers for therapeutic targeting of severe hindlimb ischemia," Biomaterials, vol. 185, 2018: pp. 360-370.
Chairoungdua et al., "Exosomes release of β-catenin: a novel mechanism that antagonizes Wnt signaling," J. Cell Biol., vol. 190, No. 6, 2010: pp. 1079-1091.
Gross and Zelarayan, "The Mingle-Mangle of Wnt Signaling and Extracellular Vesicles: Functional Implications for Heart Research," Front. Cardiovasc. Med., vol. 5, No. 10, 2018: pp. 1-8.
Urade, et al., "Endosomes differ from plasma membrane in the phospholipid molecular species composition," Biochimica et Biophysica Acta, vol. 946, 1988: pp. 161-163.
Corbo C. et al. Engineered biomimetic nanovesicles show intrinsic anti-inflammatory properties for the treatment of inflammatory bowel diseases. Nanoscale. Oct. 5, 2017;9(38):14581-14591.
Davidson et al. A model system for in vivo gene transfer into the central nervous system using an adenoviral vector. Nat. Genet. Mar. 1993;3(3):219-23.
Felgner et al. Bethesda Res. Lab. Focus. 1989 11(2):21.
G Le Gal La Salle et al. An adenovirus vector for gene transfer into neurons and glia in the brain. Science. Feb. 12, 1993;259(5097):988-90.
Glover D. et al. Oxford Univ. Press, Oxford England. 1995.
Jang S.C. et al. Bioinspired exosome-mimetic nanovesicles for targeted delivery of chemotherapeutics to malignant tumors. ACS Nano. Sep. 24, 2013;7(9):7698-710.
Kaplitt M.G., et al. Long-term gene expression and phenotypic correction using adeno-associated virus vectors in the mammalian brain. Nat. Genet. Oct. 1994;8(2):148-54.
Kleinstiver et al., High-fidelity CRISPR-Cas9 variants with undetectable genome-wide off-targets. (2016) Nature, vol. 529, No. 7587, pp. 490-495.
Lunavat T.R. et al. RNAi delivery by exosome-mimetic nanovesicles—Implications for targeting c-Myc in cancer. Biomaterials. Sep. 2016; 102:231-8.
Ma et al. Coating biomimetic nanoparticles with chimeric antigen receptor T cell-membrane provides high specificity for hepatocellular carcinoma photothermal therapy treatment. Theranostics, vol. 10, Issue 3, (2020) pp. 1281-1295.
Mannino and Gould-Fogerite. Liposome mediated gene transfer. BioTechniques. 1988;6(7):682-90.
Molinaro R. et al. Design and Development of Biomimetic Nanovesicles Using a Microfluidic Approach. Adv Mater. Apr. 2018;30(15).
Rosenfeld, et al. In vivo transfer of the human cystic fibrosis transmembrane conductance regulator gene to the airway epithelium. Cell. Jan. 10, 1992;68(1):143-55.
Sushnitha et al. Frontiers in Bioengineering and Biotechnology 8 (627): 1-17, Year: 2020.
Torres-Gomez et al. Phagocytic Integrins: Activation and Signaling (2020) Frontiers in Immunology, vol. 11, No., 738, pp. 1-10.
Yang et al. Cellular and humoral immune responses to viral antigens create barriers to lung-directed gene therapy with recombinant adenoviruses. J. Virol. Apr. 1995;69(4):2004-15.
Yue et al. Interleukin-10 Deficiency Alters Endothelial Progenitor Cell-Derived Exosome Reparative Effect on Myocardial Repair via Integrin-Linked Kinase Enrichment. (2020) Circ Res. vol. 126, No. 3, pp. 315-329.

\* cited by examiner

TAILORED HYPOIMMUNE NANOVESICULAR DELIVERY SYSTEMS FOR CANCER TUMORS

BACKGROUND OF THE INVENTION

1. Technical Field

The present invention relates to compositions and methods for delivering therapeutics and gene editing compounds.

2. Background Art

Effectively targeting in vivo delivery of gene editing therapeutics to diseased cells remains one of the greatest challenges in modern biotechnology. Even with recent improvements, delivery mechanisms consistently have inhibitory issues such as inconsistent and low frequency targeting, low targeting adaptability, lack of non-autologous approaches, high immune neutralization, high manufacturing costs, regulatory roadblocks (FDA clinical holds), low quantity production/collection/expansion, packaging size constraints, inefficient packaging, organ sinking (liver and marrow), low half-life of delivery vesicle, and IP lock-up.

AAV (adeno-associated virus) is one vector commonly used as a vector for gene editing therapeutics. AAV has a size of approximately 22 nm. AAV has a high liver sink (though lower with new mutants), limited dosing (though higher with new serotypes), size limitations of approximately 1100 amino acids, most serotypes are scalable, and targeting efficiency is limited by serotype tropism.

Liposomes can also be used as a delivery mechanism. Liposomes are 50-1000 nm in size. Organ sinking and neutralizing effects include RES (reticuloendothelial system), EPR (enhanced permeability and retention), ABC (accelerated blood clearance), CARPA (complement activation-related pseudoallergy), and opsonization. Immune neutralization varies and is ligand dependent. There are no size constraints, but active loading is necessary with most compounds which is expensive. Manufacturing can also involve ligand addition or PEGylation. Liposomes are ligand targeted and have poor tumor penetration.

Tunable dendrimers are 1.5 to 10 nm. They are highly interactive with blood proteins and have increased IgG macrophage Fc clearance. Packaging constraints include being externally conjugated nucleic acids. Tunable dendrimers have not been tested widely for use with gene editing.

Polymeric micelles are 10-100 nm in size. There are no know organ sinking or neutralization effects or immune neutralization. There may not be size constraints and they have not been tested widely for gene editing. They are ligand targeted and stimuli inducible/releasable.

Exosomes are 30-150 nm in size. Their organ sinking and neutralization effects are high but can be lower with new mutants. They have low immunogenicity, but the degree varies with each ligand. There are no size constraints, but they are very inefficient with loading. It is also difficult to produce therapeutic quantities. They are ligand targeted with average tumor penetration.

CAR T-cells have also been used to target cells to treat cancer. CAR T-cell therapy is a cancer therapy that requires the collection of a patient's own immune cells (T cells) to treat their cancer. T-cells normally attack invasive microorganisms, but in CAR T-cell therapy, the T-cells are reengineered to attack cancer cells. First, T-cells are separated from the patient's blood and genetically engineered to produce chimeric antigen receptors (CARs) on their surface that allow the T-cells to attach to a specific tumor antigen. The CARs do not exist naturally and are made up of fragments of synthetic antibodies. CARs rely on signaling and co-stimulatory domains inside the T-cell to function.

Once the CAR T-cells have been produced, they are expanded to produce large quantities that can then be infused back into the patient. Generally, the patient has undergone chemotherapy to deplete their lymphocytes prior to the infusion. The CAR T-cells are attracted to the tumor antigens on the cancer cells they are designed for and kill the cancer cells that have those antigens.

CAR T-cell therapies have been approved for the treatment of acute lymphoblastic leukemia (ALL) in children and advanced lymphomas in adults. For example, CAR T-cells that target CD-19 (tisangenlecleucel, KYMRIAH™, Novartis) have been used to treat ALL. YESCARTA™ (axicabtagene ciloleucel, Kite Pharmaceuticals) is used for lymphomas. Studies have also been conducted to target CD-22 in cells that have lost CD-19 expression. Dual targeting of CD-19 and CD-123 in leukemia has also been studied. For multiple myeloma, CAR T-cells that target BCMA have been developed. It is unclear currently whether CAR T-cells can treat solid tumors due to the microenvironment that surrounds them, but studies are being performed with targeting mesothelin expressed on pancreatic and lung cancers, and EGFRvIII expressed on glioblastoma.

There are several drawbacks to CAR T-cell therapy. It can cause cytokine release syndrome that results in high fevers and low blood pressure. This can require additional treatment with blocking IL-6 activity. It can also cause B cell die off (B cell aplasia) and require further treatment with immunoglobulins to provide antibodies. Other side effects include cerebral edema and neurotoxicity. Patients may also not have enough T-cells to harvest and engineer. Second rounds of treatment can be necessary, especially when tumor cells lose antigen expression.

Another delivery vehicle is biomimetic nanovesicles (BioNVs) or biofunctionalized liposome-like nanovesicles (BLNs), which are biologically-derived nano-sized vesicles that are similar to exosomes but larger. BioNVs have been successfully used for treatment of cancer cells with passive targeting (accumulation in tumoral tissue) Wu, et al. (2018), active targeting (functionalized nanovesicles recognize receptors in tumor cells) most recently—Zhang, et al. (2018), Goh, et al. (2017), and Lunavat, et al. (2016). Further, they have been successfully used for testing anti-inflammatory properties ($\alpha 4\beta 7$ integrin—implications inflammatory bowel disease) Corbo, et al. (2017), and hepatocyte proliferation when derived from primary hepatocytes Wu, et al. (20108). Molinaro, et al. (2018) incorporated membrane proteins within the bilayer of biomimetic nanovesicles using a microfluidic-based platform, which extended shelf-life and retained biological functions of donor cells. Jang, et al. (2013) developed bioinspired exosome-mimetic nanovesicles that deliver chemotherapeutics to the tumor tissue after systemic administration, produced by the breakdown of monocytes or macrophages using a serial extrusion through filters with diminishing pore sizes. The nanovesicles had natural targeting ability of cells by maintaining the topology of plasma membrane proteins, and chemotherapeutic drug-loaded nanovesicles trafficked to tumor tissue and reduced tumor growth.

There are several advantages to using BioNVs over exosomes. BioNVs are much easier to manufacture than collecting exosomes (which are limited when harvested from patients). BioNVs are therefore far more scalable and much easier to manufacture.

BioNVs are one option of a delivery vehicle for CRISPR Cas9 systems (U.S. Patent Application Publication Nos. 20160281111, 20170022507, 20180119123, 20180155789, 20180236103, and 20180251770). BioNVs can also be engineered by CRISPR (U.S. Patent Application Publication No. 20190085284). U.S. Patent Application Publication No. 20190060483 to Dooley, et al. discloses methods of purification of nanovesicles, and the purification can be related to surface proteins on exosomes.

There remains a need for a delivery system that can effectively deliver gene editing products and other therapeutics in the body, as well as delivery systems that can make use of CAR T-cell targeting.

SUMMARY OF THE INVENTION

The present invention provides for a method of generating biomimetic nanovesicles (BioNVs) from gene edited iPSCs by disrupting cell membranes of the gene edited iPSCs by a method of sonicating, rupturing by detergent, rupturing by enzymes, or electroporation to produce BioNVs, then purifying the BioNVs by a method of microfiltration, affinity chromatography, size exclusion chromatography, gel purification, centrifugation, or combinations thereof.

The present invention provides for BioNVs produced by the above method(s).

The present invention provides for a composition of a therapeutic agent packaged in the BioNVs for treatment of disease.

The present invention provides fora method of generating BioNVs with targeting capabilities by disrupting cell membranes of gene edited iPSCs with a targeting surface marker by a method of sonicating, rupturing by detergent, rupturing by enzymes, or electroporation.

The present invention provides for BioNVs with targeting capabilities.

The present invention also provides for a composition of a therapeutic agent packaged in BioNVs with targeting capabilities.

The present invention provides for hypoimmunogenic induced pluripotent stem cell (iPSC)-derived biomimetic nanovesicles (hypo-bioNVs) including tailored chimeric antigen receptor (CARs) which can recognize target biomarkers through an antibody fragment scFV region or by a viral epitope recognition receptor (VERR). An example of a VERR can be the vp1, vp2, or vp3 of SVV that targets TEM8 on various cancer cells. Either can be used in CAR design to allow bioNV targeting of any cell of interest. The bioNV can also encapsulate and deliver any biologic drug of choice.

The present invention provides for a method of making hypo-bioNVs.

The present invention provides for a method of treating an individual with cancer, by administering the hypo-bioNVs to an individual, targeting cancer cells, and treating the cancer.

The present invention provides for a method of targeting cells in an individual, by administering the hypo-bioNVs to an individual, and targeting cells to be destroyed or treated.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1:
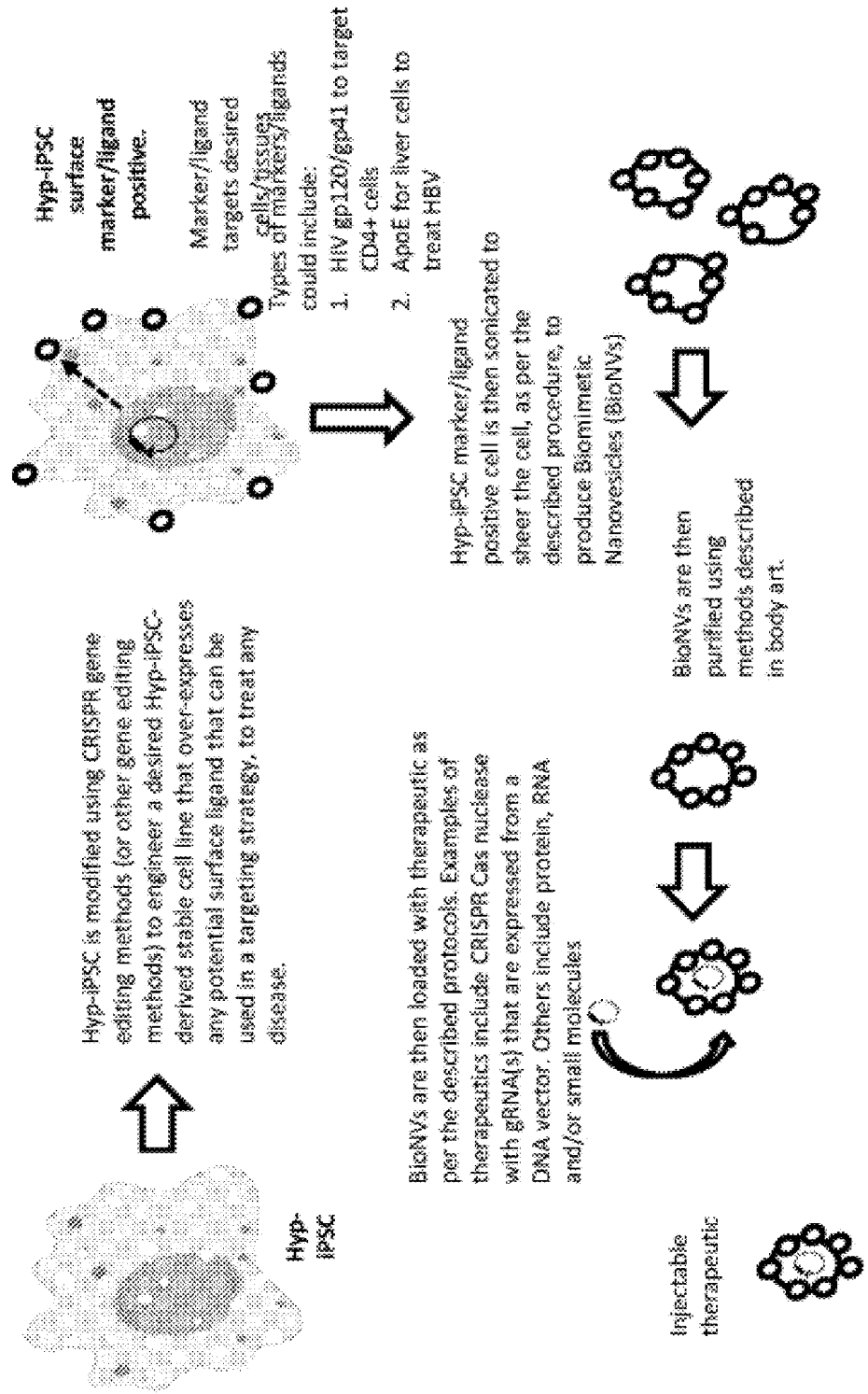
FIG. 1 is a schematic of derivation of biomimetic nanovesicles of the present invention.
Figure 2:
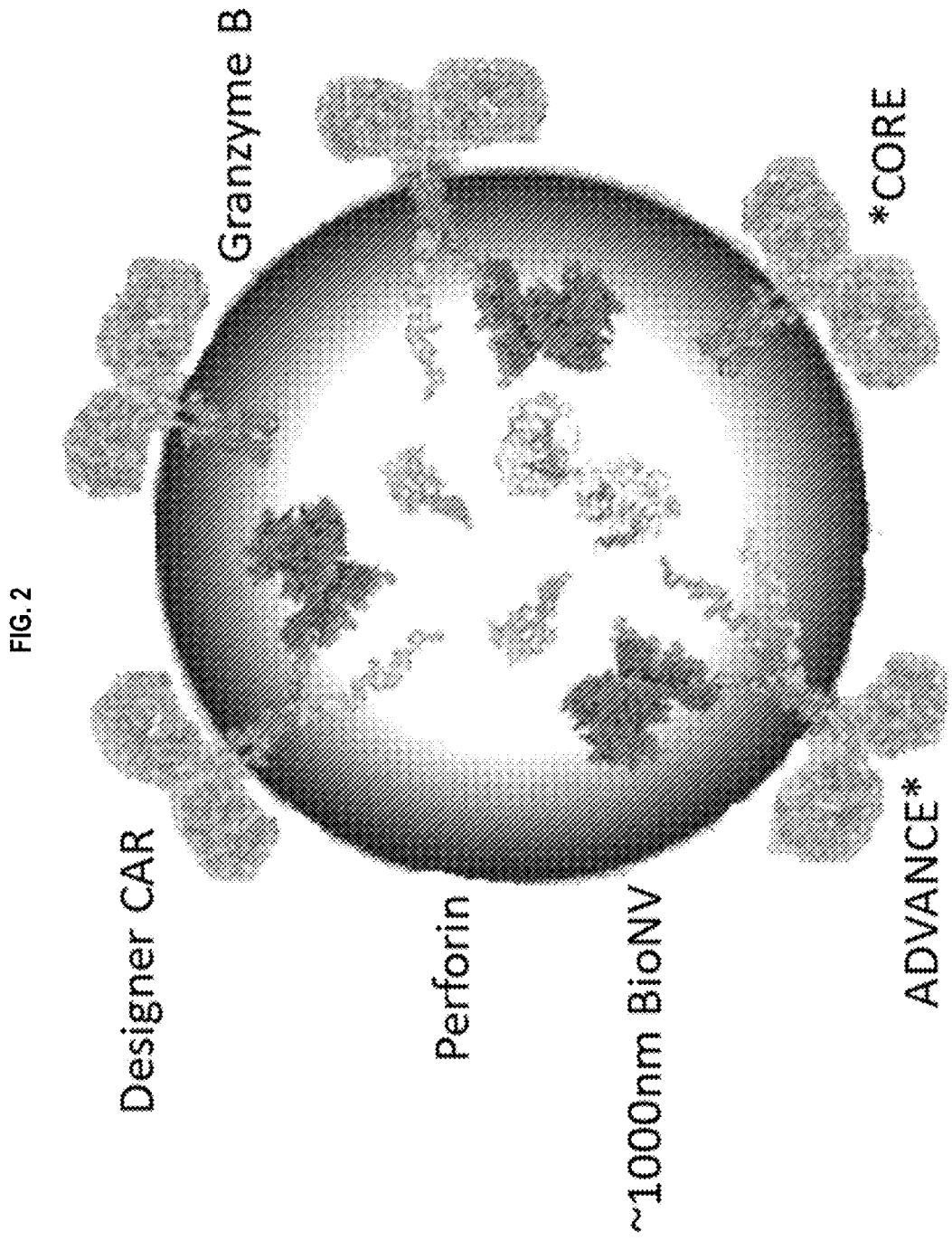
FIG. 2 is an example of a hypoimmunogenic iPSC-derived biomimetic nanovesicle (hypo-bioNV)

The present invention provides for hypoimmunogenic induced pluripotent stem cell (iPSC)-derived biomimetic nanovesicles (hypo-bioNVs) including tailored chimeric antigen receptor (CARs) which can recognize target biomarkers through an antibody fragment scFV region or by a viral epitope recognition receptor (VERR). Either can be used in CAR design to allow bioNV targeting of any cell of interest. The bioNV can also encapsulate and deliver any small molecule, biologic, nucleic, and/or gene editing therapeutic of choice to any intended cellular targets and treat diseases, especially those caused by viruses. A method of making a BioNV is shown in FIG. 1 and an example of the hypo-BioNVs is shown in FIG. 2.

"BioNV" as used herein, refers to biologically-derived nano-sized vesicles that can have designed biological functionalization.

"iPSC" as used herein refers to induced pluripotent stem cells, which are stem cells that can be generated directly from adult cells. iPSCs can propagate indefinitely and can become any cell type in the body.

The term "vector" includes cloning and expression vectors, as well as viral vectors and integrating (or non-integrating) vectors. An "expression vector" is a vector that includes a regulatory region. Vectors are also further described below.

The term "lentiviral vector" includes both integrating and non-integrating lentiviral vectors.

Viruses replicate by one of two cycles, either the lytic cycle or the lysogenic cycle. In the lytic cycle, first the virus penetrates a host cell and releases its own nucleic acid. Next, the host cell's metabolic machinery is used to replicate the viral nucleic acid and accumulate the virus within the host cell. Once enough virions are produced within the host cell, the host cell bursts (lysis) and the virions go on to infect additional cells. Lytic viruses can integrate viral DNA into the host genome as well as be non-integrated where lysis does not occur over the period of the infection of the cell.

"Lysogenic virus" as used herein, refers to a virus that replicates by the lysogenic cycle (i.e. does not cause the host cell to burst and integrates viral nucleic acid into the host cell DNA). The lysogenic virus can mainly replicate by the lysogenic cycle but sometimes replicate by the lytic cycle. In the lysogenic cycle, virion DNA is integrated into the host cell, and when the host cell reproduces, the virion DNA is copied into the resulting cells from cell division. In the lysogenic cycle, the host cell does not burst. Lysogenic viruses treated with the compositions and methods of the present invention can include, but are not limited to, hepatitis A, hepatitis B, hepatitis D, HSV-1, HSV-2, cytomegalovirus, Epstein-Barr virus, Varicella Zoster virus, HIV1, HIV2, HTLV1, HTLV2, Rous Sarcoma virus, HPV virus, yellow fever, zika, dengue, West Nile, Japanese encephalitis, lyssa virus, vesiculovirus, cytohabdovirus, Hantaan virus, Rift Valley virus, Bunyamwera virus, Lassa virus, Junin virus, Machupo virus, Sabia virus, Tacaribe virus, Flexal virus, Whitewater Arroyo virus, ebola, Marburg virus, JC virus, and BK virus.

"Lytic virus" as used herein refers to a virus that replicates by the lytic cycle (i.e. causes the host cell to burst after an accumulation of virus within the cell). The lytic virus can mainly replicate by the lytic cycle but sometimes replicate by the lysogenic cycle. Lytic viruses treated by the compositions and methods of the present invention can include, but are not limited to, hepatitis A, hepatitis C, hepatitis D, coxsachievirus, HSV-1, HSV-2, cytomegalovirus, Epstein-Barr virus, varicella zoster virus, HIV1, HIV2, HTLV1, HTLV2, Rous Sarcoma virus, rota, seadornvirus, coltivirus, JC virus, and BK virus.

The compositions of the present invention can be used to treat infections caused by either active or latent viruses. The compositions of the present invention can be used to treat individuals in which latent virus is present, but the individual has not yet presented symptoms of the virus. The compositions can target virus in any cells in the individual, such as, but not limited to, CD4+ lymphocytes, macrophages, fibroblasts, monocytes, T lymphocytes, B lymphocytes, natural killer cells, dendritic cells such as Langerhans cells and follicular dendritic cells, hematopoietic stem cells, endothelial cells, brain microglial cells, and gastrointestinal epithelial cells.

"gRNA" as used herein refers to guide RNA. The gRNAs in the CRISPR Cas systems and other CRISPR nucleases herein are used for engineering CAR T cells. This is accomplished by using one or more specifically designed gRNAs to avoid the issues seen with single gRNAs such as mutations. The gRNA can be a sequence complimentary to a coding or a non-coding sequence and can be tailored to the particular sequence to be targeted. The gRNA can be a sequence complimentary to a protein coding sequence, for example, a sequence encoding one or more viral structural proteins. The gRNA sequence can be a sense or anti-sense sequence. It should be understood that when a gene editor composition is administered herein, preferably (but not limited to) this includes two or more gRNAs; however, a single gRNA can also be used.

"Nucleic acid" as used herein, refers to both RNA and DNA, including cDNA, genomic DNA, synthetic DNA, and DNA (or RNA) containing nucleic acid analogs, any of which may encode a polypeptide of the invention and all of which are encompassed by the invention. Polynucleotides can have essentially any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA) and portions thereof, transfer RNA, ribosomal RNA, siRNA, micro-RNA, short hairpin RNA (shRNA), interfering RNA (RNAi), ribozymes, cDNA, recombinant polynucleotides, branched polynucleotides, plasmids, vectors, isolated DNA of any sequence, isolated RNA of any sequence, nucleic acid probes, and primers, as well as nucleic acid analogs. In the context of the present invention, nucleic acids can encode a benign surface marker whose expression is regulated by viral (for clearing virally infected cells) or epigenetic regulatory elements (for clearing cancer cells).

An "isolated" nucleic acid can be, for example, a naturally-occurring DNA molecule or a fragment thereof, provided that at least one of the nucleic acid sequences normally found immediately flanking that DNA molecule in a naturally-occurring genome is removed or absent. Thus, an isolated nucleic acid includes, without limitation, a DNA molecule that exists as a separate molecule, independent of other sequences (e.g., a chemically synthesized nucleic acid, or a cDNA or genomic DNA fragment produced by the polymerase chain reaction (PCR) or restriction endonuclease treatment). An isolated nucleic acid also refers to a DNA molecule that is incorporated into a vector, an autonomously replicating plasmid, a virus, or into the genomic DNA of a prokaryote or eukaryote. In addition, an isolated nucleic acid can include an engineered nucleic acid such as a DNA molecule that is part of a hybrid or fusion nucleic acid. A nucleic acid existing among many (e.g., dozens, or hundreds to millions) of other nucleic acids within, for example, cDNA libraries or genomic libraries, or gel slices containing a genomic DNA restriction digest, is not an isolated nucleic acid.

Isolated nucleic acid molecules can be produced by standard techniques. For example, polymerase chain reaction (PCR) techniques can be used to obtain an isolated nucleic acid containing a nucleotide sequence described herein, including nucleotide sequences encoding a polypeptide described herein. PCR can be used to amplify specific sequences from DNA as well as RNA, including sequences from total genomic DNA or total cellular RNA. Various PCR methods are described in, for example, PCR Primer: A Laboratory Manual, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >50-100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring portion of a Cas9-encoding DNA (in accordance with, for example, the formula above).

More specifically, the present invention provides for a method of generating bionanovesicles (BioNVs) from gene-edited iPSCs by disrupting cell membranes of the gene edited iPSCs by sonicating, rupturing the cells by detergent, rupturing the cells by enzymes (such as by trypsinization), or using electroporation. It should be understood that while sonication is further referred to below, any of the above methods can be used in disrupting cell membranes. BioNVs are generally membranes enclosing an internal space that can be used for transporting therapeutic agents. The method includes inducing vesicle budding with mild detergent treatment in a shaker, low-speed centrifugation to collect the vesicles, and Covaris sonication (vesicle sizing and loading). Analysis can be performed with Malvern Zetasizing and flow cytometry. The present invention also provides for the BioNVs produced by this method. The BioNVs can be 20-1000 nm in diameter.

Most preferably, the gene-edited iPSCs are CRISPR modified iPSCs and hypoimmunogenic (Hypo-iPSCs), such as those described in Deuse, et al. (Nature Biotechnology, Vol. 37, March 2019, p. 252-258). These iPSCs have been modified to inactivate MHC class I and II genes and overexpress CD47 such that the resulting iPSCs are allogenic and do not cause an immune reaction in patients they are administered to. Therefore, BioNVs derived from such iPSCs are useable in all patients. Various gene editing methods (further described below) can be used to create the iPSC cells instead of CRISPR/Cas9, such as, but not limited to, TALENs, ZFNs, RNase P RNA, C2c1, C2c2, C2c3, Cas9, Cpf1, TevCas9, Archaea Cas9, CasY.1, CasY.2, CasY.3, CasY.4, CasY.5, CasY.6, or CasX. As shown in FIG. 1, Hypo-iPSCs are modified using CRISPR or other gene editing methods to engineer a desired Hypo-iPSC-derived stable cell line that overexpresses any potential surface ligand that can be used in a targeting strategy to treat any disease. The Hypo-iPSCs can include surface markers or ligands that target desired cells or tissues, such as, but not limited to, HIV gp120/gp41 to target CD4+ cells, ApoE for liver cells to treat HBV, or CARs or VERRs for various cancer and/or virally-infected cellular targets. The Hypo-iPSC marker/ligand positive cells are then sonicated to shear the cells to produce BioNVs, purified by a method of microfiltration, affinity chromatography, size exclusion chromatography, gel purification, centrifugation, or combinations thereof, and 1. loaded with therapeutics (such as, but not limited to, CRISPR Cas nuclease with gRNA(s) that are expressed from a DNA vector, protein, RNA, and/or small molecules) 2. Pre-loaded by expressing CRISPR Cas nucleases and/or gRNAs from a chromosomally-integrated and stable 'gene editing cassette' (that can be regulated by drugs such as tetracycline—Tet On/Off systems). The result is an injectable therapeutic.

The BioNVs are therefore scalable using the sonication process and no longer personalized. Previous methods deriving BioNVs from PBMCs (using the sonication FAF method) from individual patients provided a personalized approach of BioNV manufacture and development, and this method would be limited to individual patients due to immuno-responses that would occur in cross patient populations, and therefore commercially inviable. The present invention solves this problem by providing BioNVs that can be used in all patient populations.

The present invention has several advantages over the prior art. By using allogeneic iPSCs as the source for BioNV derivation, the BioNVs can be engineered to be loaded with any ligand that can target a desired receptor. The allogeneic iPSC can be engineered to over express any ligand that in turn can recognize any receptor. Once the ligand-loaded allogeneic iPSC is engineered, the BioNVs are then derived from the cell line, packaged with the correct vector therapeutic (such as CRISPR Cas nucleases and gRNAs on a DNA vector), then delivered to the targeted cell.

The present invention also provides for a composition of a therapeutic agent packaged in BioNVs for treatment of disease, such as diseases caused by viruses and cancers. The therapeutic agent can be, but is not limited to, DNA, plasmid DNA, RNA, protein, or combinations thereof. The composition can be made by sonication, transfection or electroporation methods. The therapeutic agent is deliverable to any target and BioNV delivery can be systemic since the BioNV was derived from an iPSC without any surface markers.

The present invention also provides for BioNVs with targeting capabilities and a method of making BioNVs with targeting capabilities. Using standard cell line development protocols, and using the CRISPR (or other gene editor)-modified allogenic iPSCs, a stable cell line can be developed where the surface marker of the desired target organ or cell type (for example ApoE for liver cell targeting), is constitutively expressed (from a strong promoter such as CMV etc.) within the CRISPR-modified allogeneic iPSC. The expression of the desired surface marker allows for the iPSCs to present the surface marker on its cellular membrane. Once the surface marker is expressed on the cellular membrane of the CRISPR-modified allogeneic iPSCs (the 'target capable' iPSC cell line), the BioNVs are then derived from the cell line using the sonication protocols as above. The BioNVs now have the surface marker coated on them (for example ApoE for liver cell targeting), thereby giving them targeting properties.

The present invention also provides for a composition of a therapeutic agent packaged in BioNVs with targeting capabilities. The therapeutic agents can be packaged in the BioNVs as described above.

The compositions herein can be used to treat any of the viruses (diseases caused by them) described above, whether lysogenic or lytic or both. The composition can also be used to treat various undesired cell types, such as pre-cancerous cells, cancer cells, or cancer cells caused by viruses.

Figure 3:
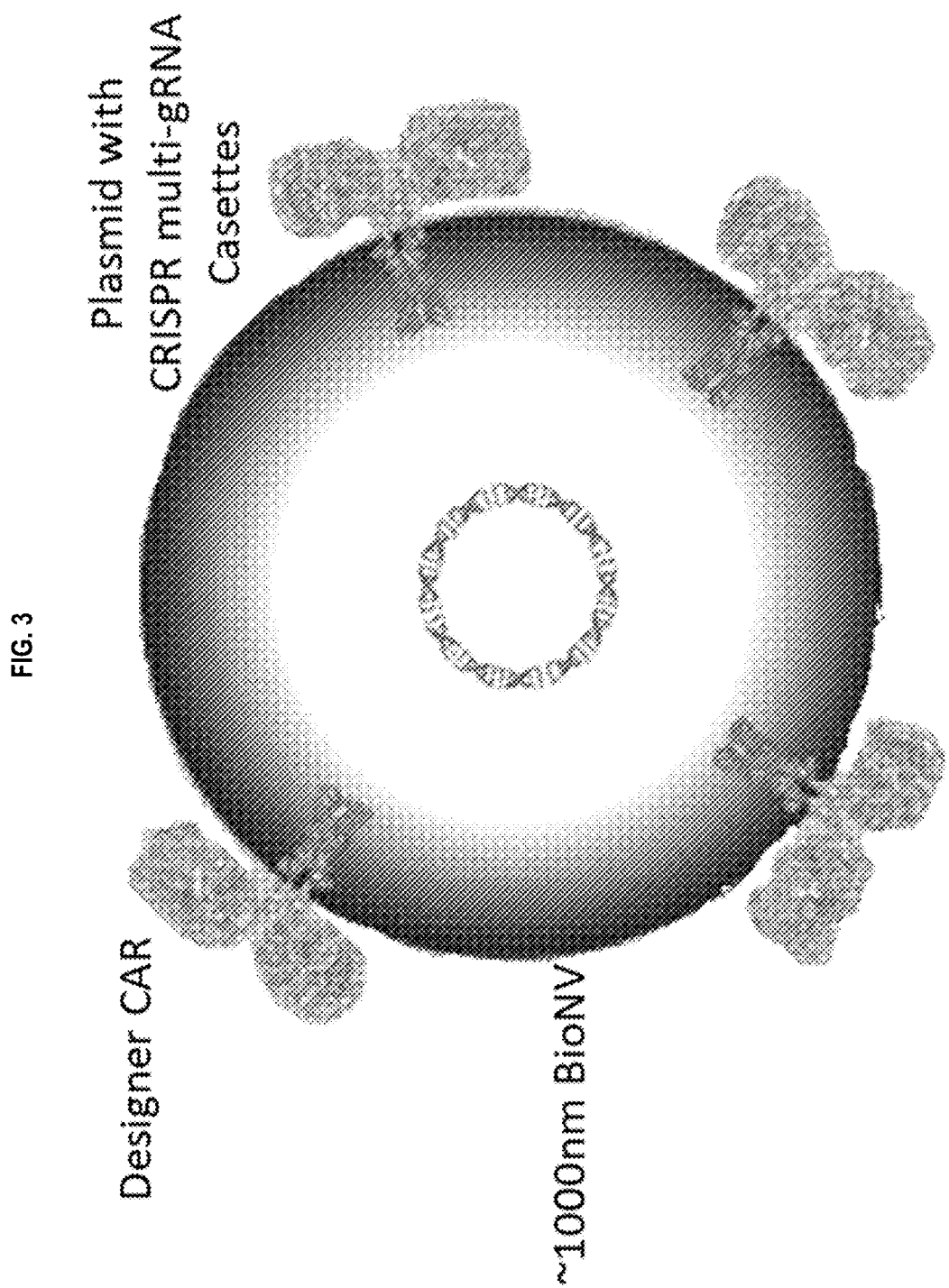
FIG. 3 is an example of a hypo-bioNV for use in gene editing.

The hypo-bioNVs can also be loaded with any CRISPR-gRNA (or gene editor) expression plasmid therapeutic for efficient and corrective gene therapy. An example is shown in FIG. 3.

CRISPR Cas9 gene editing has been used to create hypo-immunogenic hiPSC cell lines derived from human CD34+ cord blood. This CD34+ cord blood derived cell line serves as a base source for bioNV development, production, and manufacture for the delivery of gene editing therapeutics for hereditary disease, and anti-cancer therapeutics to the micro-environment of cancer cells. Deuse, et al. (2019) extensively tested the CD34+ cord blood-derived hypo-immunogenic cell line to confirm the low expression of HLA 1/2 and overexpression of CD47. Once confirmed, the cells were additionally tested for their hypo-immune phenotypes in humanized mice studies. Compared to a wildtype cell line that causes INF-γ expression, an IgM reaction, and the activation of NK cells, the hypo-immunogenic iPSCs do not elicit any of these responses. Each of these experiments was duplicated (with similar results) when the iPSC line was differentiated to cardiomyocytes and epithelial cells.

CAR T-cells have been shown to be an excellent source of biomimetic nanovesicles that contain CAR surface receptors. CAR-coated BioNVs have been shown to have several key advantages over stand alone CAR T-cell therapies. Deuse, et al. reported that they have potent anti-cancer properties without the occurrence of cytokine storms or runaway cytotoxicity. They have accessibility to the tumor microenvironment without the loss of function and tumor penetration. There is zero transfer of genetic information that can lead to teratoma formation. There are multi-target capabilities for single cancer type or multiple cancers simultaneously.

Fu, et al. (2019) reported that CAR T-cells have been shown to shed exosomes (typically 10× smaller than BNVs) that contain equivalent concentrations of CAR receptors on their surface while containing high levels of cytotoxic molecules that inhibit tumor growth. Fu, et al. showed that CAR T-cells release about 7-8 fold higher concentrations of exosomes when they are stimulated with antigen. Immunoblot analysis showed the concentrations of CAR on the surface of CAR T-cells from whole cell extracts and exosomes derived from CAR T-cells stimulated with CD28/CD3 beads or cancer cell antigen stimulation. Exosomal CAR binds to cancer antigen in a concentration dependent manner and this interaction can be disrupted with blocking antibody CTX (cetuximab) and TTZ (trastuzumab). Fu, et al. also showed that CAR exosomes have anti-tumor activity in various types of cancers. CAR-EXO-CTX (CAR exosomes with cetuximab scFv) and CAR-EXO-TTZ (CAR exosomes with trastuzumab scFv) show significant tumor reduction in mouse xenograft models containing breast cancer and lung adenocarcinoma tumors, in an increasing CAR-EXO concentration dependent manner. Patient-derived tumor tissue fragments that were established as subcutaneous xenografts were treated with 100 µg doses of CAR-EXO-TTZ show considerable tumor inhibition in HER2-positive breast and ovary cancer models.

In the present invention, critical gene subtractions and additions can be created in the hypo-immunogenic iPSCs in an HLA1/HLA2 null cell line derived from CD34+ cord blood.

B2M-/-→HLA1 hypo-immune
CIITA-/-→HLA2 hypo-immune
CD47-/-→CD47 null (restored phagocytosis)
PD1-/-→PDL1 resistance elimination An upstream CRISPRa CAR expression cassette with Cpf1 guided nuclease swap out system can be used to make alterations to the genes.

Figure 4:
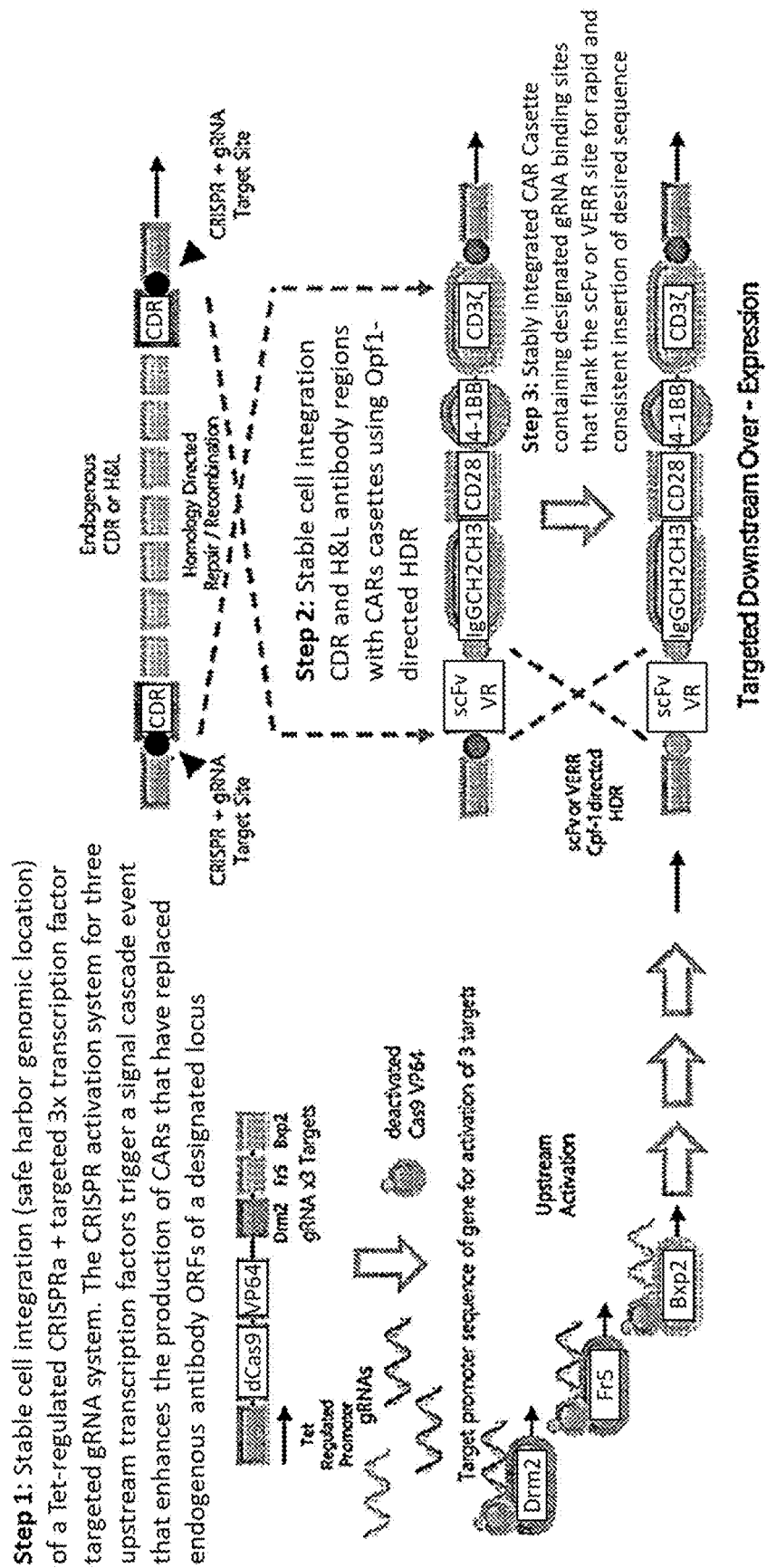
FIG. 4 is a schematic showing how the hypo-bioNVs are made.

The hypo-bioNVs of the present invention can be made as follows, and as shown in the diagram in FIG. 4. First there is stable cell integration (safe harbor genomic location) of a drug-regulated (such as Tet-regulated) CRISPRa+targeted 3× transcription factor targeted gRNA system (Drm2, Fr5, Bxp2—genes that have been shown to upregulate antibody production). The CRISPR activation system for three upstream transcription factors trigger a signal cascade event that enhances the productions of CARs that have replaced endogenous antibody ORFs at a designated locus. Next, there is stable replacement of CDR and H&L antibody regions with CAR cassettes using Cpf1-directed (or any other CRISPR Cas/ZFN, TALEN) HDR. Once the CAR cassette is stably integrated, the scFV and VERR regions of the cassette (near the 5' end of the cassette) can be 'swapped out' for any desired scFV or VERR using Cpf1-directed (or any other CRISPR Cas/ZFN, TALEN) HDR.

Figure 5:
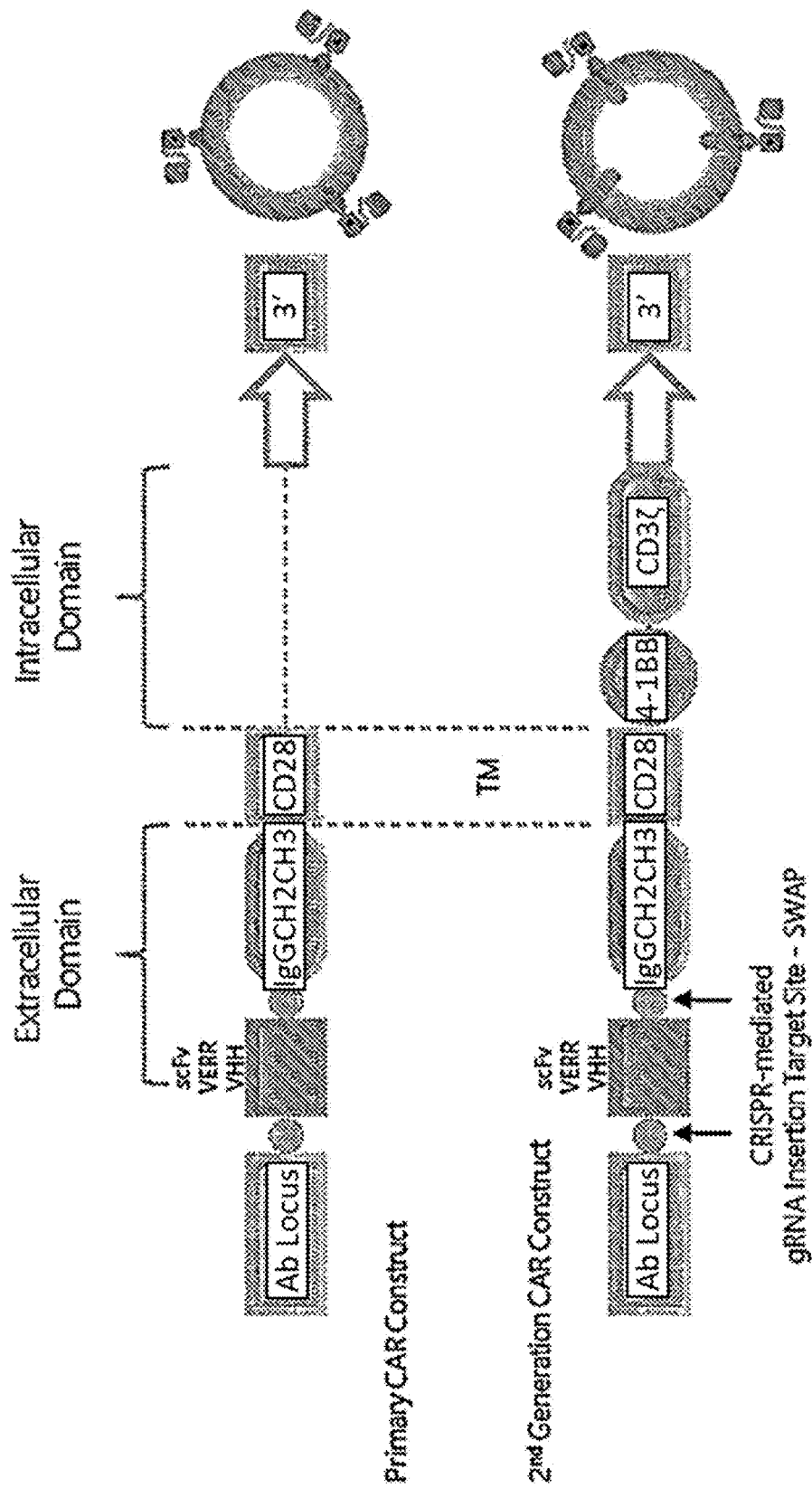
FIG. 5 is a schematic of two different bioNVs.

This method can be used to create hypo-bioNVs with different functions, as shown in FIG. 5, which details how to express first generation versus second generation CARs on the surface of the hypo-bioNVs. For example, one type of hypo-bioNV can be derived solely from a targeted cell line that expresses CAR (scFV or VERR) surface ligands only. These cell lines can be further adapted to express essential and tailored proteins or nucleic acids that can be packaged in the end-result bioNV. Another type of hypo-bioNV can be derived from a targeted cell line that contains the intracellular CAR (scFV or VERR) components necessary for the activation of lymphocytic granular and cytokine responses. Further, this foundation cell line can be differentiated from its pluripotent state into a desired lymphocyte (T-cell, NK, macrophage), from which the bioNVs can then be derived. The resulting bioNVs are surface coated with 2nd generation CAR (scFV or VERR) ligands and loaded with factors that elicit tumor killing.

Cell lines can be designed to express any protein and/or nucleic acid therapeutic with anti-cancer or anti-viral properties as shown in TABLE 1.

TABLE 1

| Modification | Phenotype |
|---|---|
| B2M -/- CIITA -/- | HLA1/HLA2 hypo-immunity |
| CD47 -/- | Phagocytic-enabled |
| PD1 -/- | PDL1 resistance elimination |
| CORE Primary CAR Expression Cassette | Specific biomarker targeting |
| ↑↑ Perforin & Granzyme B Expression | Tumor cytotoxicity/apoptosis |
| Fas Ligand +ve | Induces apoptosis |
| ↑↑ NCAM (optional) | Cell adhesion (neural & hematopoietic) |
| Option Therapeutic Expression | Specific Drug Action |

This can eliminate the need for the over-expression and pre-packaging of biologic therapeutics. Cell lines developed using this process contains a second-generation CAR ligand that is necessary for lymphocyte activation. Once the desired CAR ligand is expressed, the cell line is differentiated into a CAR-lymphocyte, activated with the appropriate antigen, then processed to produce 'loaded and targeted' bioNVs. Cell lines can have modifications listed in TABLE 2.

TABLE 2

| Modification | Phenotype |
|---|---|
| B2M -/- CIITA -/- | HLA1/HLA2 hypo-immunity |
| CD47 -/- | Phagocytic-enabled |
| PD1 -/- | PDL1 resistance elimination |
| ADVANCE 2nd Gen CAR Expression Cassette | Specific biomarker targeting with Lymphocyte Activation |
| Lymphocyte Activation Modifications N/A | Activated Lymphocyte loaded BioNVs |

Figure 6:
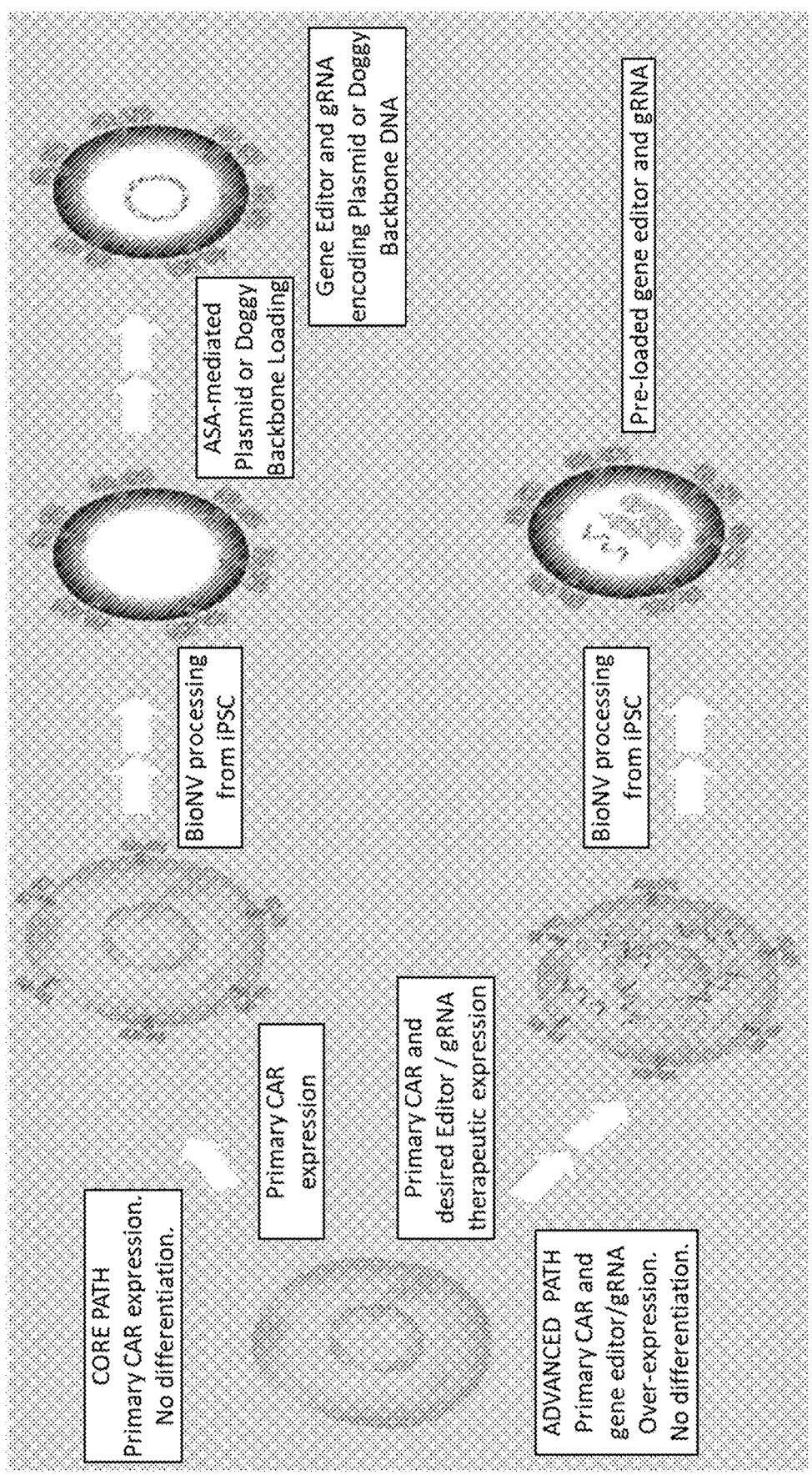
FIG. 6 is a schematic of two paths of bioNVs.

FIG. 6 shows methods of making bioNVs in the context of first generation versus second generation CARs on the surface of bioNVs in the context of delivering various types of drugs or cytokines. In one path, there is CAR and protein expression only and no differentiation. There is primary CAR and desired protein therapeutic expression. There is bioNV processing from iPSC. BioNVs contain primary surface CARs and essential (but limited) lymphocyte activating proteins=perforin and Granzyme B. No antigen activation is required, and additional anti-cancer drugs can be added.

Figure 7:
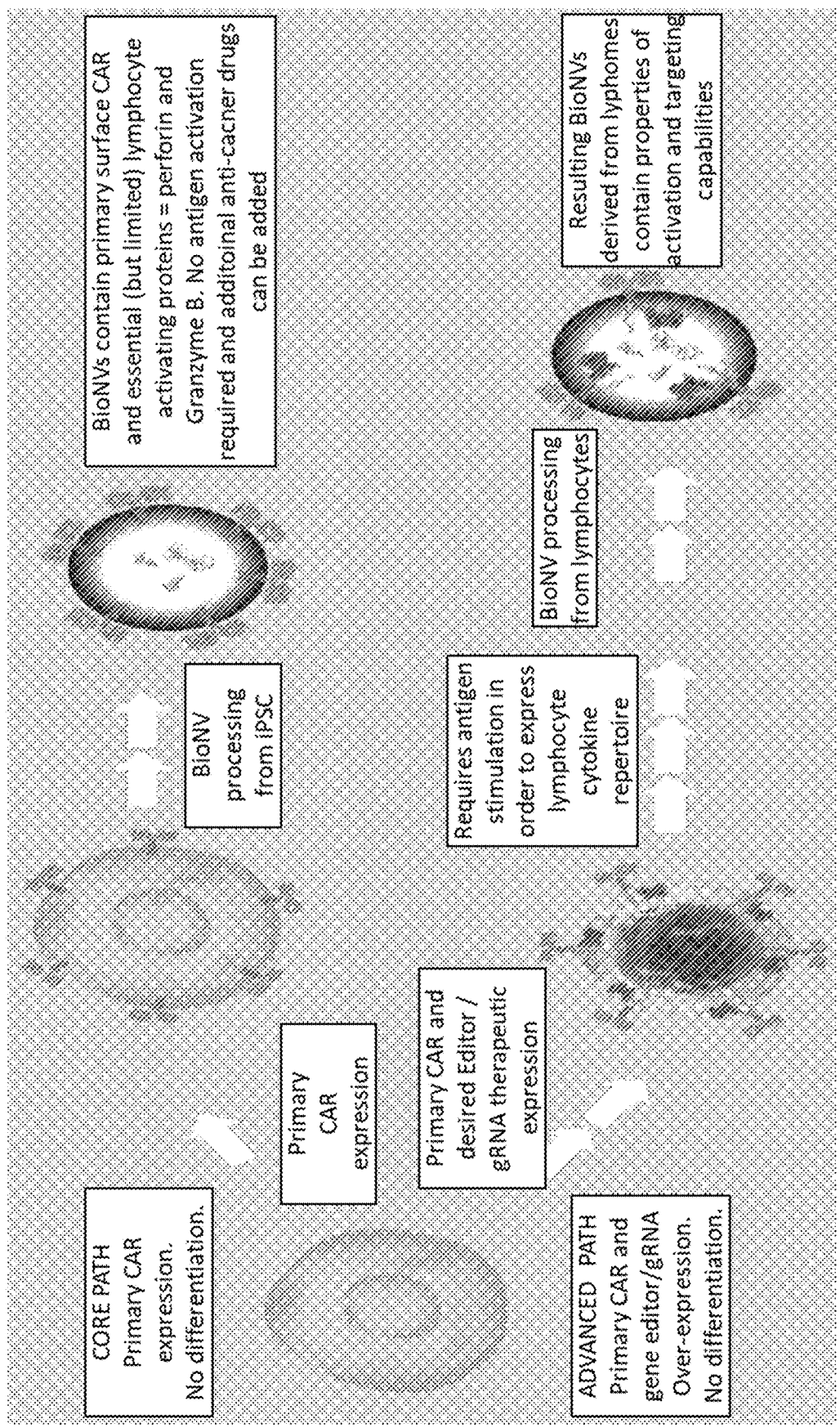
FIG. 7 is a schematic of two paths of bioNVs.

In another path in FIG. 7, there is iPSC differentiation into lymphocyte cell lines, and this requires no packaging. There is second generation CAR expression. Antigen stimulation is required in order to express lymphocyte cytokine repertoire. There is bioNV processing from lymphocytes. Resulting bioNVs derived from the lymphocytes contain properties of activation and targeting capabilities.

Modifications can be made as in TABLE 3. There is hypo-immunogenicity of the base iPSC, by engineering critical gene subtractions and additions into an HLA1/HLA2 null cell line derived from CD34+ cord blood.

TABLE 3

| Modification | Phenotype |
|---|---|
| B2M -/- | HLA1 hypo-immunity |
| CIITA -/- | HLA2 hypo-immunity |
| CD47 -/- | Phagocytic-enabled |
| PD1 -/- | PDL1 resistance elimination |
| ↑↑ NCAM (optional) | Cell adhesion (neural & hematopoietic) |

TABLE 3-continued

| Modification | Phenotype |
| --- | --- |
| CAR Expression Cassette | Specific biomarker targeting |
| CRISPR nuclease/gRNA Expression Cassette | Gene Editing |

FIG. 7 shows two paths for making bioNVs for the delivery of gene editing therapeutics. In one path, there is CAR and protein expression and no differentiation. There is primary (first generation) CAR expression. There is bioNV processing from iPSC. There is ASA-mediated plasmid or doggy backbone loading. There is gene editor and gRNA encoding plasmid or doggy backbone DNA that is inserted into the bioNVs via electroporation or sonication.

In another path in FIG. 7, there is primary (first generation) CAR and gene editor/gRNA over-expression and no differentiation. There is primary CAR and desired editor/gRNA therapeutic expression. There is bioNV processing from iPSC. There is pre-loaded gene editor and gRNA that is expressed from a stable integrated and drug inducible 'gene editing cassette'.

Figure 8:
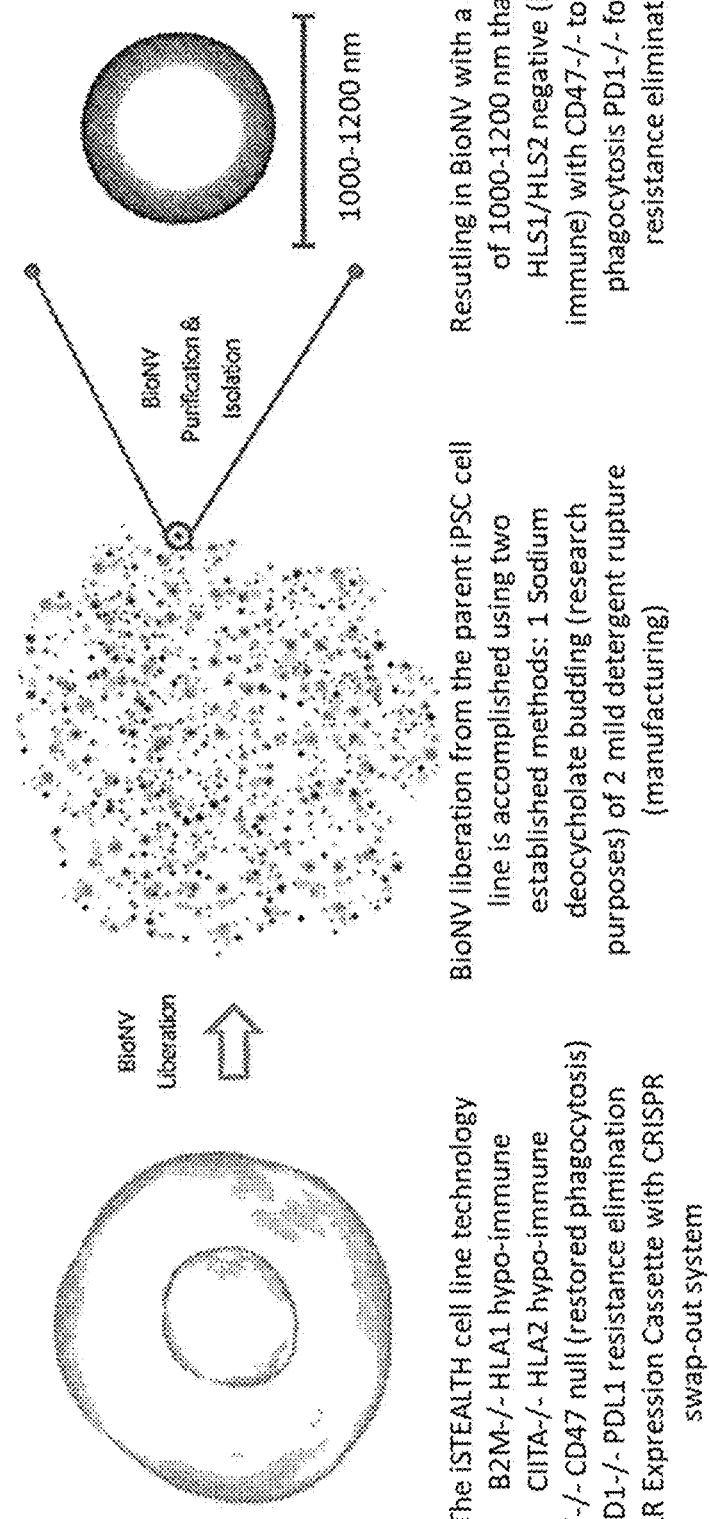
FIG. 8 is a schematic of a manufacturing process.

FIG. 8 shows a manufacturing process for the hypo-bioNVs. There is BNV liberation from the parent iPSC cell line that is accomplished using two established methods—1) sodium deoxycholate budding (research purposes) or 2) mild detergent rupture (manufacturing). This results in hypo-bioNVs with a size range of 1000-1200 nm that are HLA1/HLA2 negative (hypo-immune) with, CD47−/− to promote phagocytosis, PD1−/− for PDL1 resistance elimination.

Figure 9:
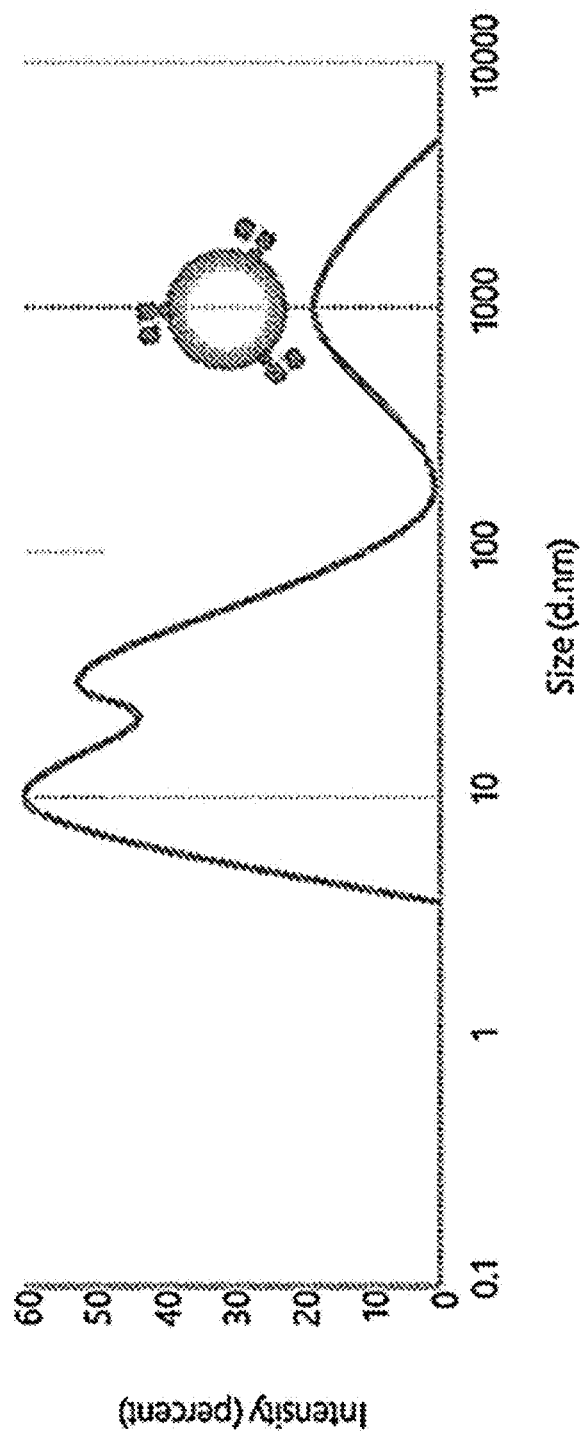
FIG. 9 is a graph of size distribution.
Figure 10:
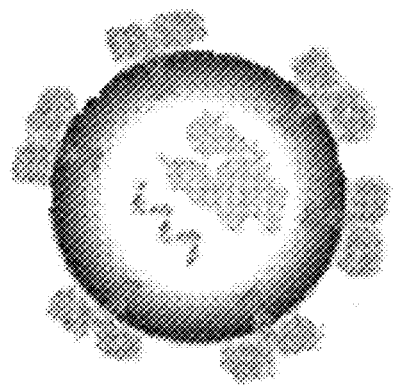
FIG. 10 shows examples of hypo-bioNVs.
Figure 10:
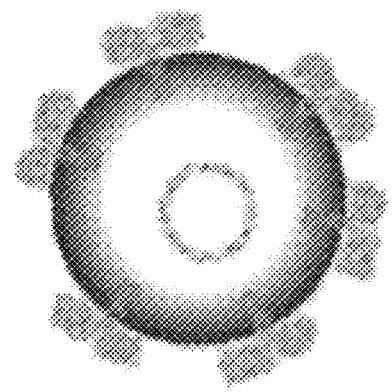
Figure 10:
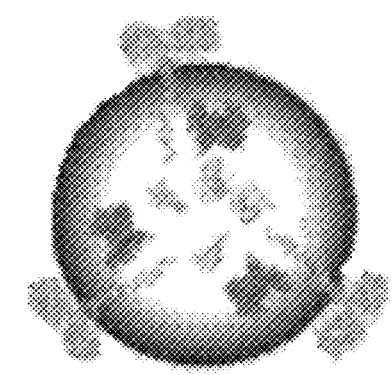
Figure 10:
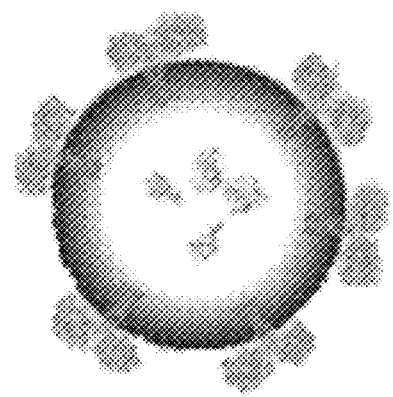

FIG. 9 shows size distribution by intensity. Zetasizer Nano ZS measured particle sizes in solution by laser light scattering. This sample shows three peaks: 1)~12 nm=protein aggregates, 2)~50 nm=subcellular debris, membrane fragments, and 3)~1000 nm=tailored nanovesicles. FIG. 10 shows examples of bioNVs.

The hypo-bioNVs can contain various therapeutics such as gene editors of TALENs, ZFNs, RNase P RNA, C2c1, C2c2, C2c3, Cas9, Cpf1, TevCas9, Archaea Cas9, CasY.1, CasY.2, CasY.3, CasY.4, CasY.5, CasY.6, or CasX. The gene editors can also include gRNA, which as used herein refers to guide RNA. The gRNA can be a sequence complimentary to a coding or a non-coding sequence and can be tailored to the particular sequence to be targeted. The gRNA can be a sequence complimentary to a protein coding sequence, for example, a sequence encoding one or more viral structural proteins, (e.g., gag, pol, env and tat). The gRNA sequence can be a sense or anti-sense sequence. It should be understood that when a gene editor composition is administered herein, preferably (but not limited to) this includes two or more gRNAs; however, a single gRNA can also be used.

The present invention provides for a method of treating an individual with cancer, by administering the hypo-bioNVs to an individual, targeting cancer cells, and treating the cancer. The CAR receptor (that may consist of either an scFV or VERR region) can recognize its specific biomarker on the cancer cell. Once the CAR docks/interacts with the biomarker on the cancer cell (the target), it releases its payload (drug, cytokine, peptide, gene editor/gRNA, plasmid etc.)

The hypo-bioNVs can target cancer cells associated with adenoid cystic carcinoma, adrenal gland tumors, a myloidosis, anal cancer, appendix cancer, astrocytoma, ataxia-telangiectasia, attenuated familial adenomatous polyposis, Beckwith-Wiedermann Syndrome, bile duct cancer, Birt-Hogg-Dube Syndrome, bladder cancer, bone cancer, brain stem glioma, brain tumors, breast cancer, carcinoid tumors, Carney complex, central nervous system tumors, cervical cancer, colorectal cancer, Cowden syndrome, craniopharyngioma, desmoplastic infantile ganglioglioma, endocrine tumors, ependymoma, esophageal cancer, Ewing sarcoma, eye cancer, eyelid cancer, fallopian tube cancer, familial adenomatous polyposis, familial malignant melanoma, familial non-VHL clear cell renal cell carcinoma, gallbladder cancer, Gardner Syndrome, gastrointestinal stromal tumor, germ cell tumor, gestational trophoblastic disease, head and neck cancer, diffuse gastric cancer, leiomyomatosis and renal cell cancer, mixed polyposis syndrome, pancreatitis, papillary renal cell carcinoma, HIV and AIDS-related cancer, islet cell tumors, juvenile polyposis syndrome, kidney cancer, lacrimal gland tumor, laryngeal and hypopharyngeal cancer, acute lymphoblastic leukemia, acute lymphocytic leukemia, acute myeloid leukemia, B-cell prolymphocytic leukemia, hairy cell leukemia, chronic lymphocytic leukemia, chronic myeloid leukemia, chronic T-cell lymphocytic leukemia, eosinophilic leukemia, Li-Fraumeni Syndrome, liver cancer, lung cancer, Hodgkin lymphoma, Non-Hodgkin lymphoma, Lynch Syndrome, mastocytosis, medulloblastoma, melanoma, meningioma, mesothelioma, Muir-Torre Syndrome, multiple endocrine neoplasia type 1, multiple endocrine neoplasia type 2, multiple myeloma, myelodysplastic syndromes, MYH-associated polyposis, nasal cavity and paranasal sinus cancer, nasopharyngeal cancer, neuroblastoma, neuroendocrine tumors, neurofibromatosis type 1, neurofibromatosis type 2, nevoid basal cell carcinoma syndrome, oral and oropharyngeal cancer, osteosarcoma, ovarian cancer, pancreatic cancer, parathyroid cancer, penile cancer, Peutz-Jeghers Syndrome, pituitary gland tumors, pleuropulmonary blastoma, prostate cancer, retinoblastoma, rhabdomyosarcoma, salivary gland cancer, sarcoma, alveolar soft part and cardiac sarcoma, Kaposi sarcoma, skin cancer, small bowel cancer, stomach cancer, testicular cancer, thymoma, thyroid cancer, tuberous sclerosis syndrome, Turcot Syndrome, unknown primary, uterine cancer, vaginal cancer, Von Hippel-Lindau Syndrome, Wilms tumors, or Xeroderma pigmentosum.

The present invention provides for a method of targeting cells in an individual, by administering the hypo-bioNVs to an individual, and targeting cells to be destroyed or treated. The CAR receptor (that may consist of either an scFV or VERR region) can recognize its specific biomarker on the cell to be destroyed or treated. Once the CAR docks/interacts with the biomarker on the cell (the target), it releases its payload (drug, cytokine, peptide, gene editor/gRNA, plasmid etc.) The bioNVs can enter the tumor microenvironment without being deactivated and can deliver their payloads with more efficiency that other methods.

The hypo-bioNVs encapsulate the key potent components of activated T-cells. Unlike CAR therapies that have limited efficacy in the tumor micro-environment, the hypo-bioNVs of the present invention overcome this issue by packing a lymphocyte punch to diseased cells without side effects associated with current approaches. The hypo-bioNVs eliminate cytokine storm potential, they provide stable and tailored targeted access to any tumor micro-environment, and they have a higher efficacy of tumor penetration than other delivery systems. The hypo-bioNVs have the advantages of high frequency and tailored targeting, they are highly adaptable, they are off the shelf allogeneic, they have hypo-immunity, they allow for high quality manufacturing and scalability, and uniform and targeted biodistribution.

The gene editors that can be used in engineering the iPSCs are as follows. Once the iPSCs are constructed, gene editor expression cassettes (may or may not be drug regulated) can also be incorporated stably. The iPSC line will now have a gene editor expression cassette that can be turned on. Once turned on, the editor (and gRNAs) will be over-expressed in the cell. The cell is then treated to produce bioNVs and the bioNVs now have the gene editor with the desired gRNA packaged in them, for delivery as a therapeutic to its intended cell target. Any gene editor listed below will work in this capacity.

Zinc finger nuclease (ZFN) creates double-strand breaks at specific DNA locations. A ZFN has two functional domains, a DNA-binding domain that recognizes a 6 bp DNA sequence, and a DNA-cleaving domain of the nuclease Fok I.

TALENs (transcription activator-like effector nucleases) include a TAL effector DNA-binding domain fused to a DNA cleavage domain that create double strand breaks in DNA.

Human WRN is a RecQ helicase encoded by the Werner syndrome gene. It is implicated in genome maintenance, including replication, recombination, excision repair and DNA damage response. These genetic processes and expression of WRN are concomitantly upregulated in many types of cancers. Therefore, it has been proposed that targeted destruction of this helicase could be useful for elimination of cancer cells. Reports have applied the external guide sequence (EGS) approach in directing an RNase P RNA to efficiently cleave the WRN mRNA in cultured human cell lines, thus abolishing translation and activity of this distinctive 3'-5' DNA helicase-nuclease.

The Class 2 type VI-A CRISPR/Cas effector "C2c2" demonstrates an RNA-guided RNase function and can be packaged and delivered as a therapeutic in the iPSCs through cassettes as described above. C2c2 from the bacterium *Leptotrichia shahii* provides interference against RNA phage. In vitro biochemical analysis show that C2c2 is guided by a single crRNA and can be programmed to cleave ssRNA targets carrying complementary protospacers. In bacteria, C2c2 can be programmed to knock down specific mRNAs. Cleavage is mediated by catalytic residues in the two conserved HEPN domains, mutations in which generate catalytically inactive RNA-binding proteins. The RNA-focused action of C2c2 complements the CRISPR-Cas9 system, which targets DNA, the genomic blueprint for cellular identity and function. The ability to target only RNA, which helps carry out the genomic instructions, offers the ability to specifically manipulate RNA in a high-throughput manner—and manipulate gene function more broadly. These results demonstrate the capability of C2c2 as a new RNA-targeting tools.

Another Class 2 type V-B CRISPR/Cas effector "C2c1" can also be used in the present invention for editing DNA. C2c1 contains RuvC-like endonuclease domains related distantly to Cpf1 (described below). C2c1 can target and cleave both strands of target DNA site-specifically. According to Yang, et al. (PAM-Dependent Target DNA Recognition and Cleavage by C2c1 CRISPR-Cas Endonuclease, Cell, 2016 Dec. 15; 167(7):1814-1828)), a crystal structure confirms *Alicyclobacillus acidoterrestris* C2c1 (AacC2c1) binds to sgRNA as a binary complex and targets DNAs as ternary complexes, thereby capturing catalytically competent conformations of AacC2c1 with both target and non-target DNA strands independently positioned within a single RuvC catalytic pocket. Yang, et al. confirms that C2c1-mediated cleavage results in a staggered seven-nucleotide break of target DNA, crRNA adopts a pre-ordered five-nucleotide A-form seed sequence in the binary complex, with release of an inserted tryptophan, facilitating zippering up of 20-bp guide RNA:target DNA heteroduplex on ternary complex formation, and that the PAM-interacting cleft adopts a "locked" conformation on ternary complex formation.

C2c3 is a gene editor effector of type V-C that is distantly related to C2c1, and contains RuvC-like nuclease domains. C2c3 is also similar to the CasY.1-CasY.6 group described below.

"CRISPR Cas9" as used herein refers to Clustered Regularly Interspaced Short Palindromic Repeat (CRISPR)-associated endonuclease Cas9. In bacteria the CRISPR/Cas loci encode RNA-guided adaptive immune systems against mobile genetic elements (viruses, transposable elements and conjugative plasmids). Three types (I-III) of CRISPR systems have been identified. CRISPR clusters contain spacers, the sequences complementary to antecedent mobile elements. CRISPR clusters are transcribed and processed into mature CRISPR (Clustered Regularly Interspaced Short Palindromic Repeats) RNA (crRNA). The CRISPR-associated endonuclease, Cas9, belongs to the type II CRISPR/Cas system and has strong endonuclease activity to cut target DNA. Cas9 is guided by a mature crRNA that contains about 20 base pairs (bp) of unique target sequence (called spacer) and a trans-activated small RNA (tracrRNA) that serves as a guide for ribonuclease III-aided processing of pre-crRNA. The crRNA:tracrRNA duplex directs Cas9 to target DNA via complementary base pairing between the spacer on the crRNA and the complementary sequence (called protospacer) on the target DNA. Cas9 recognizes a trinucleotide (NGG) protospacer adjacent motif (PAM) to specify the cut site (the 3rd nucleotide from PAM). The crRNA and tracrRNA can be expressed separately or engineered into an artificial fusion small guide RNA (sgRNA) via a synthetic stem loop (AGAAAU) to mimic the natural crRNA/tracrRNA duplex. Such sgRNA, like shRNA, can be synthesized or in vitro transcribed for direct RNA transfection or expressed from U6 or H1-promoted RNA expression vector, although cleavage efficiencies of the artificial sgRNA are lower than those for systems with the crRNA and tracrRNA expressed separately.

CRISPR/Cpf1 is a DNA-editing technology analogous to the CRISPR/Cas9 system, characterized in 2015 by Feng Zhang's group from the Broad Institute and MIT. Cpf1 is an RNA-guided endonuclease of a class II CRISPR/Cas system. This acquired immune mechanism is found in *Prevotella* and *Francisella* bacteria. It prevents genetic damage from viruses. Cpf1 genes are associated with the CRISPR locus, coding for an endonuclease that use a guide RNA to find and cleave viral DNA. Cpf1 is a smaller and simpler endonuclease than Cas9, overcoming some of the CRISPR/Cas9 system limitations. CRISPR/Cpf1 could have multiple applications, including treatment of genetic illnesses and degenerative conditions.

A CRISPR/TevCas9 system can also be used. In some cases, it has been shown that once CRISPR/Cas9 cuts DNA in one spot, DNA repair systems in the cells of an organism will repair the site of the cut. The TevCas9 enzyme was developed to cut DNA at two sites of the target so that it is harder for the cells' DNA repair systems to repair the cuts (Wolfs, et al., Biasing genome-editing events toward precise length deletions with an RNA-guided TevCas9 dual nuclease, PNAS, doi:10.1073). The TevCas9 nuclease is a fusion of a I-Tevi nuclease domain to Cas9.

The Cas9 nuclease can have a nucleotide sequence identical to the wild type *Streptococcus pyrogenes* sequence. In some embodiments, the CRISPR-associated endonuclease can be a sequence from other species, for example other *Streptococcus* species, such as *Thermophilus; Psuedomona aeruginosa, Escherichia coli*, or other sequenced bacteria genomes and archaea, or other prokaryotic microorganisms. Alternatively, the wild type *Streptococcus pyrogenes* Cas9 sequence can be modified. The nucleic acid sequence can be codon optimized for efficient expression in mammalian cells, i.e., "humanized." A humanized Cas9 nuclease sequence can be for example, the Cas9 nuclease sequence encoded by any of the expression vectors listed in Genbank accession numbers KM099231.1 GI:669193757; KM099232.1 GI:669193761; or KM099233.1 GI:669193765. Alternatively, the Cas9 nuclease sequence can be for example, the sequence contained within a commercially available vector such as PX330 or PX260 from Addgene (Cambridge, MA). In some embodiments, the Cas9 endonuclease can have an amino acid sequence that is a variant or a fragment of any of the Cas9 endonuclease sequences of Genbank accession numbers KM099231.1 GI:669193757; KM099232.1 GI:669193761; or KM099233.1 GI:669193765 or Cas9 amino acid sequence of PX330 or PX260 (Addgene, Cambridge, MA). The Cas9 nucleotide sequence can be modified to encode biologically active variants of Cas9, and these variants can have or can include, for example, an amino acid sequence that differs from a wild type Cas9 by virtue of containing one or more mutations (e.g., an addition, deletion, or substitution mutation or a combination of such mutations). One or more of the substitution mutations can be a substitution (e.g., a conservative amino acid substitution). For example, a biologically active variant of a Cas9 polypeptide can have an amino acid sequence with at least or about 50% sequence identity (e.g., at least or about 50%, 55%, 60%, 65%, 70%, 75%, 80%, 85%, 90%, 95%, 97%, 98%, or 99% sequence identity) to a wild type Cas9 polypeptide. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. The amino acid residues in the Cas9 amino acid sequence can be non-naturally occurring amino acid residues. Naturally occurring amino acid residues include those naturally encoded by the genetic code as well as non-standard amino acids (e.g., amino acids having the D-configuration instead of the L-configuration). The present peptides can also include amino acid residues that are modified versions of standard residues (e.g. pyrrolysine can be used in place of lysine and selenocysteine can be used in place of cysteine). Non-naturally occurring amino acid residues are those that have not been found in nature, but that conform to the basic formula of an amino acid and can be incorporated into a peptide. These include D-alloisoleucine (2R,3S)-2-amino-3-methylpentanoic acid and L-cyclopentyl glycine (S)-2-amino-2-cyclopentyl acetic acid. For other examples, one can consult textbooks or the worldwide web (a site is currently maintained by the California Institute of Technology and displays structures of non-natural amino acids that have been successfully incorporated into functional proteins). The Cas-9 can also be any shown in TABLE 4 below.

TABLE 4

| Variant No. | Four Alanine Substitution Mutants (compared to WT Cas9) | Tested* |
|---|---|---|
| 1 | SpCas9 N497A, R661A, Q695A, Q926A | YES |
| 2 | SpCas9 N497A, R661A, Q695A, Q926A + D1135E | YES |
| 3 | SpCas9 N497A, R661A, Q695A, Q926A + L169A | YES |
| 4 | SpCas9 N497A, R661A, Q695A, Q926A + Y450A | YES |
| 5 | SpCas9 N497A, R661A, Q695A, Q926A + M495A | Predicted |
| 6 | SpCas9 N497A, R661A, Q695A, Q926A + M694A | Predicted |
| 7 | SpCas9 N497A, R661A, Q695A, Q926A + H698A | Predicted |
| 8 | SpCas9 N497A, R661A, Q695A, Q926A + D1135E + L169A | Predicted |
| 9 | SpCas9 N497A, R661A, Q695A, Q926A + D1135E + Y450A | Predicted |
| 10 | SpCas9 N497A, R661A, Q695A, Q926A + D1135E + M495A | Predicted |
| 11 | SpCas9 N497A, R661A, Q695A, Q926A + D1135E + M694A | Predicted |
| 12 | SpCas9 N497A, R661A, Q695A, Q926A + D1135E + M698A | Predicted |
| | Three Alanine Substitution Mutants (compared to WT Cas9) | Tested* |
| 13 | SpCas9 R661A, Q695A, Q926A | No (on target only) |
| 14 | SpCas9 R661A, Q695A, Q926A + D1135E | Predicted |
| 15 | SpCas9 R661A, Q695A, Q926A + L169A | Predicted |
| 16 | SpCas9 R661A, Q695A, Q926A + Y450A | Predicted |
| 17 | SpCas9 R661A, Q695A, Q926A + M495A | Predicted |
| 18 | SpCas9 R661A, Q695A, Q926A + M694A | Predicted |
| 19 | SpCas9 R661A, Q695A, Q926A + H698A | Predicted |
| 20 | SpCas9 R661A, Q695A, Q926A + D1135E + L169A | Predicted |
| 21 | SpCas9 R661A, Q695A, Q926A + D1135E + Y450A | Predicted |
| 22 | SpCas9 R661A, Q695A, Q926A + D1135E + M495A | Predicted |
| 23 | SpCas9 R661A, Q695A, Q926A + D1135E + M694A | Predicted |

Although the RNA-guided endonuclease Cas9 has emerged as a versatile genome-editing platform, some have reported that the size of the commonly used Cas9 from *Streptococcus pyogenes* (SpCas9) limits its utility for basic research and therapeutic applications that use the highly versatile adeno-associated virus (AAV) delivery vehicle. Accordingly, the six smaller Cas9 orthologues have been used and reports have shown that Cas9 from *Staphylococcus aureus* (SaCas9) can edit the genome with efficiencies similar to those of SpCas9, while being more than 1 kilobase shorter. SaCas9 is 1053 bp, whereas SpCas9 is 1358 bp.

The Cas9 nuclease sequence, or any of the gene editor effector sequences described herein, can be a mutated sequence. For example, the Cas9 nuclease can be mutated in the conserved HNH and RuvC domains, which are involved in strand specific cleavage. For example, an aspartate-to-alanine (D10A) mutation in the RuvC catalytic domain allows the Cas9 nickase mutant (Cas9n) to nick rather than cleave DNA to yield single-stranded breaks, and the subsequent preferential repair through HDR can potentially decrease the frequency of unwanted indel mutations from off-target double-stranded breaks. In general, mutations of the gene editor effector sequence can minimize or prevent off-targeting.

The gene editor effector can also be Archaea Cas9. The size of Archaea Cas9 is 950aa ARMAN 1 and 967aa ARMAN 4. The Archaea Cas9 can be derived from ARMAN-1 (*Candidatus* Micrarchaeum acidiphilum ARMAN-1) or ARMAN-4 (*Candidatus* Parvarchaeum acidiphilum ARMAN-4).

Any of the gene editor effectors herein can also be tagged with Tev or any other suitable homing protein domains. According to Wolfs, et al. (Proc Natl Acad Sci USA. 2016 Dec. 27; 113(52):14988-14993. doi: 10.1073/pnas.1616343114. Epub 2016 Dec. 12), Tev is an RNA-guided dual active site nuclease that generates two noncompatible DNA breaks at a target site, effectively deleting the majority of the target site such that it cannot be regenerated.

Vectors containing nucleic acids such as those described herein also are provided. A "vector" is a replicon, such as a plasmid, phage, or cosmid, into which another DNA segment may be inserted to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. Numerous vectors and expression systems are commercially available from such corporations as Novagen (Madison, WI), Clontech (Palo Alto, CA), Stratagene (La Jolla, CA), and Invitrogen/Life Technologies (Carlsbad, CA).

The vectors provided herein also can include, for example, origins of replication, scaffold attachment regions (SARs), and/or markers. A marker gene can confer a selectable phenotype on a host cell. For example, a marker can confer biocide resistance, such as resistance to an antibiotic (e.g., kanamycin, G418, bleomycin, or hygromycin). As noted above, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, CT) sequences typically are expressed as a fusion with the encoded polypeptide. Such tags can be inserted anywhere within the polypeptide, including at either the carboxyl or amino terminus.

Additional expression vectors also can include, for example, segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX, pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2μ plasmid or derivatives thereof, vectors useful in eukaryotic cells, such as vectors useful in insect or mammalian cells; vectors derived from combinations of plasmids and phage DNAs, such as plasmids that have been modified to employ phage DNA or other expression control sequences.

The vector can also include a regulatory region. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, nuclear localization signals, and introns.

As used herein, the term "operably linked" refers to positioning of a regulatory region and a sequence to be transcribed in a nucleic acid to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

Vectors include, for example, viral vectors (such as adenoviruses ("Ad"), adeno-associated viruses (AAV), and vesicular stomatitis virus (VSV) and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al; *BioTechniques*, 34: 167-171 (2003). A large variety of such vectors are known in the art and are generally available.

A "recombinant viral vector" refers to a viral vector comprising one or more heterologous gene products or sequences. Since many viral vectors exhibit size-constraints associated with packaging, the heterologous gene products or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying gene products necessary for replication and/or encapsidation). Modified viral vectors in which a polynucleotide to be delivered is carried on the outside of the viral particle have also been described (see, e.g., Curiel, D T, et al. *PNAS* 88: 8850-8854, 1991).

Suitable nucleic acid delivery systems include recombinant viral vector, typically sequence from at least one of an adenovirus, adenovirus-associated virus (AAV), helper-dependent adenovirus, retrovirus, or hemagglutinating virus of Japan-liposome (HVJ) complex. In such cases, the viral vector comprises a strong eukaryotic promoter operably linked to the polynucleotide e.g., a cytomegalovirus (CMV) promoter. The recombinant viral vector can include one or more of the polynucleotides therein, preferably about one polynucleotide. In some embodiments, the viral vector used in the invention methods has a pfu (plague forming units) of from about $10^8$ to about $5 \times 10^{10}$ pfu. In embodiments in which the polynucleotide is to be administered with a non-viral vector, use of between from about 0.1 nanograms to about 4000 micrograms will often be useful e.g., about 1 nanogram to about 100 micrograms.

Additional vectors include viral vectors, fusion proteins and chemical conjugates. Retroviral vectors include Moloney murine leukemia viruses and HIV-based viruses. One HIV-based viral vector comprises at least two vectors wherein the gag and pol genes are from an HIV genome and the env gene is from another virus. DNA viral vectors include pox vectors such as orthopox or avipox vectors, herpesvirus vectors such as a herpes simplex I virus (HSV) vector [Geller, A. I. et al., *J. Neurochem,* 64: 487 (1995); Lim, F., et al., in DNA Cloning: Mammalian Systems, D. Glover, Ed. (Oxford Univ. Press, Oxford England) (1995); Geller, A. I. et al., *Proc Natl. Acad. Sci.*: U.S.A.:90 7603 (1993); Geller, A. I., et al., *Proc Natl. Acad. Sci* USA: 87:1149 (1990)], Adenovirus Vectors [LeGal LaSalle et al., *Science,* 259:988 (1993); Davidson, et al., *Nat. Genet.* 3: 219 (1993); Yang, et al., *J. Virol.* 69: 2004 (1995)] and Adeno-associated Virus Vectors [Kaplitt, M. G., et al., *Nat. Genet.* 8:148 (1994)].

Pox viral vectors introduce the gene into the cell's cytoplasm. Avipox virus vectors result in only a short-term expression of the nucleic acid. Adenovirus vectors, adeno-associated virus vectors and herpes simplex virus (HSV) vectors may be an indication for some invention embodiments. The adenovirus vector results in a shorter-term expression (e.g., less than about a month) than adeno-associated virus, in some embodiments, may exhibit much longer expression. The particular vector chosen will depend upon the target cell and the condition being treated. The selection of appropriate promoters can readily be accomplished. An example of a suitable promoter is the 763-base-pair cytomegalovirus (CMV) promoter. Other suitable promoters which may be used for gene expression include, but are not limited to, the Rous sarcoma virus (RSV) (Davis, et al., Hum Gene Ther 4:151 (1993)), the SV40 early promoter region, the herpes thymidine kinase promoter, the regulatory sequences of the metallothionein (MMT) gene, prokaryotic expression vectors such as the β-lactamase promoter, the tac promoter, promoter elements from yeast or other fungi such as the GAL4 promoter, the ADH (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells, insulin gene control region which is active in pancreatic beta cells, immunoglobulin gene control region which is active in lymphoid cells, mouse mammary tumor virus control region which is active in testicular, breast, lymphoid and mast cells, albumin gene control region which is active in liver, alpha-fetoprotein gene control region which is active in liver, alpha 1-antitrypsin gene control region which is active in the liver, beta-globin gene control region which is active in myeloid cells, myelin basic protein gene control region which is active in oligodendrocyte cells in the brain, myosin light chain-2 gene control region which is active in skeletal muscle, and gonadotropic releasing hormone gene control region which is active in the hypothalamus. Certain proteins can be expressed using their native promoter. Other elements that can enhance expression can also be included such as an enhancer or a system that results in high levels of expression such as a tat gene and tar element. This cassette can then be inserted into a vector, e.g., a plasmid vector such as, pUC19, pUC118, pBR322, or other known plasmid vectors, that includes, for example, an *E. coli* origin of replication. See, Sambrook, et al., Molecular Cloning: A Laboratory Manual, Cold Spring Harbor Laboratory press, (1989). The plasmid vector may also include a selectable marker such as the β-lactamase gene for ampicillin resistance, provided that the marker polypeptide does not adversely affect the metabolism of the organism being treated. The cassette can also be bound to a nucleic acid binding moiety in a synthetic delivery system, such as the system disclosed in WO 95/22618.

If desired, the polynucleotides of the invention can also be used with a microdelivery vehicle such as cationic liposomes and adenoviral vectors. For a review of the procedures for liposome preparation, targeting and delivery of contents, see Mannino and Gould-Fogerite, *BioTechniques,* 6:682 (1988). See also, Feigner and Holm, Bethesda Res. Lab. Focus, 11(2):21 (1989) and Maurer, R. A., Bethesda Res. Lab. Focus, 11(2):25 (1989).

Replication-defective recombinant adenoviral vectors can be produced in accordance with known techniques. See, Quantin, et al., *Proc. Natl. Acad. Sci. USA,* 89:2581-2584 (1992); Stratford-Perricadet, et al., J. Clin. Invest., 90:626-630 (1992); and Rosenfeld, et al., Cell, 68:143-155 (1992).

Another delivery method is to use single stranded DNA producing vectors which can produce the expressed products intracellularly. See for example, Chen et al, *BioTechniques,* 34: 167-171 (2003), which is incorporated herein, by reference, in its entirety.

As described above, the compositions of the present invention can be prepared in a variety of ways known to one of ordinary skill in the art. Regardless of their original source or the way they are obtained, the compositions of the invention can be formulated in accordance with their use. For example, the nucleic acids and vectors described above can be formulated within compositions for application to cells in tissue culture or for administration to a patient or subject. Any of the pharmaceutical compositions of the invention can be formulated for use in the preparation of a medicament, and particular uses are indicated below in the context of treatment, e.g., the treatment of a subject having a virus or at risk for contracting a virus. When employed as pharmaceuticals, any of the nucleic acids and vectors can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intra-arterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

This invention also includes pharmaceutical compositions which contain, as the active ingredient, nucleic acids and vectors described herein in combination with one or more pharmaceutically acceptable carriers. The terms "pharmaceutically acceptable" (or "pharmacologically acceptable") refer to molecular entities and compositions that do not produce an adverse, allergic or other untoward reaction when administered to an animal or a human, as appropriate. The methods and compositions disclosed herein can be applied to a wide range of species, e.g., humans, non-human primates (e.g., monkeys), horses or other livestock, dogs, cats, ferrets or other mammals kept as pets, rats, mice, or other laboratory animals. The term "pharmaceutically acceptable carrier," as used herein, includes any and all solvents, dispersion media, coatings, antibacterial, isotonic and absorption delaying agents, buffers, excipients, binders, lubricants, gels, surfactants and the like, that may be used as media for a pharmaceutically acceptable substance. In making the compositions of the invention, the active ingredient is typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), lotions, creams, ointments, gels, soft and hard gelatin capsules, suppositories, sterile injectable solutions, and sterile packaged powders. As is known in the art, the type of diluent can vary depending upon the intended route of administration. The resulting compositions can include additional agents, such as preservatives. In some embodiments, the carrier can be, or can include, a lipid-based or polymer-based colloid. In some embodiments, the carrier material can be a colloid formulated as a liposome, a hydrogel, a microparticle, a nanoparticle, or a block copolymer micelle. As noted, the carrier material can form a capsule, and that material may be a polymer-based colloid.

The bioNVs may also be applied to a surface of a device (e.g., a catheter) or contained within a pump, patch, or other drug delivery device. The nucleic acids and vectors of the invention can be administered alone, or in a mixture, in the presence of a pharmaceutically acceptable excipient or carrier (e.g., physiological saline). The excipient or carrier is selected based on the mode and route of administration. Suitable pharmaceutical carriers, as well as pharmaceutical necessities for use in pharmaceutical formulations, are described in Remington's Pharmaceutical Sciences (E. W. Martin), a well-known reference text in this field, and in the USP/NF (United States Pharmacopeia and the National Formulary).

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

The invention claimed is:

1. A hypoimmunogenic induced pluripotent stem cell (iPSC)-derived biomimetic nanovesicle (hypo-BioNV) comprising a surface coated with one or more chimeric antigen receptor (CAR) comprising an antibody single chain variable fragment (scFv) or a viral epitope recognition receptor (VERR),
wherein the hypo-BioNV is comprised of cell membrane of a gene-edited hypoimmunogenic iPSC,
wherein the gene-edited hypoimmunogenic iPSC, and hypo-bioNV derived therefrom, is HLA1 negative, HLA2 negative, PD1 negative, and CD47 negative,
wherein the hypo-BioNV recognizes one or more target biomarkers through the antibody fragment scFv region or VERR, and
wherein the hypo-BioNV encapsulates and is capable of delivering one or more of a small molecule, biologic, nucleic acid, and/or gene editing therapeutic to a cellular target that expresses the one or more target biomarkers.

2. The hypo-BioNV of claim 1, wherein the hypo-BioNV surface further comprises Fas Ligand and/or neural cell adhesion molecule (NCAM).

3. The hypo-BioNV of claim 1, wherein the hypo-BioNV encapsulates perforin, granzyme, or perforin and granzyme.

4. The hypo-BioNV of claim 1, wherein the iPSC is derived from CD34+ cord blood.

5. The hypo-BioNV of claim 1, wherein the nucleic acid comprises one or more gene, gene fragment, exon, intron, messenger RNA (mRNA), transfer RNA, ribosomal RNA, siRNA, micro-RNA, short hairpin RNA (shRNA), interfering RNA (RNAi), ribozyme, cDNA, recombinant polynucleotides, branched polynucleotides, plasmid, vector, isolated DNA, isolated RNA, nucleic acid probe, nucleic acid primer, and nucleic acid analog.

6. The hypo-BioNV of claim 1, wherein the gene editing therapeutic comprises one or more gRNA or a plasmid encoding the one or more gRNA.

7. The hypo-BioNV of claim 1, wherein the gene editing therapeutic comprises one or more of a transcription activator-like effector nuclease (TALEN), zinc finger nuclease (ZFN), RNase P RNA, C2c1, C2c2, C2c3, Cas9, Cpf1, TevCas9, Archaea Cas9, CasY.1, CasY.2, CasY.3, CasY.4, CasY.5, CasY.6, or CasX.

8. The hypo-BioNV of claim 1, wherein the hypo-BioNV has a size of 300 nm to 1000 nm, or wherein the hypo-BioNV has a size of 1000 nm to 1200 nm.

9. The hypo-BioNV of claim 1, wherein the VERR comprises vp1, vp2, or vp3 of SVV.

10. The hypo-BioNV of claim 1, wherein the hypo-BioNV comprises a surface having HIV gp120/gp41 or ApoE.

11. A hypoimmunogenic induced pluripotent stem cell (iPSC)-derived biomimetic nanovesicle (hypo-BioNV) comprising a surface coated with one or more chimeric antigen receptor (CAR) comprising an antibody single chain variable fragment (scFv) or a viral epitope recognition receptor (VERR),
   wherein the hypo-bioNV is comprised of cell membrane of a gene-edited hypoimmunogenic iPSC,
   wherein the gene-edited hypoimmunogenic iPSC, and hypo-bioNV derived therefrom, is HLA1 negative, HLA2 negative, and PD1 negative, and lacks CD47,
   wherein the hypo-BioNV has a size of 300 nm to 1000 nm or 1000 nm to 1200 nm,
   wherein the hypo-BioNV recognizes one or more target biomarkers through the antibody fragment scFv or VERR, and
   wherein the hypo-BioNV encapsulates and is capable of delivering one or more of perforin and granzyme to a cellular target that expresses the one or more target biomarkers.

12. The hypo-BioNV of claim 11, wherein the hypo-BioNV a surface further comprises Fas Ligand and/or neural cell adhesion molecule (NCAM).

13. The hypo-BioNV of claim 11, wherein the iPSC is derived from CD34+ cord blood.

14. The hypo-BioNV of claim 11, wherein the hypo-BioNV encapsulates perforin.

15. The hypo-BioNV of claim 11, wherein the hypo-BioNV encapsulates granzyme.

16. The hypo-BioNV of claim 11, wherein the hypo-BioNV further encapsulates a gene editing therapeutic comprising one or more gRNA or a plasmid encoding the one or more gRNA.

17. The hypo-BioNV of claim 11, wherein the hypo-BioNV has a size of 300 nm to 1000 nm.

18. The hypo-BioNV of claim 11, wherein the hypo-BioNV has a size of 1000 nm to 1200 nm.

19. The hypo-BioNV of claim 11, wherein the VERR comprises vp1, vp2, or vp3 of SVV.

20. The hypo-BioNV of claim 11, wherein the VERR comprises HIV gp120 and gp41, or wherein the hypo-BioNV surface further comprises ApoE.

* * * * *